United States Patent [19]

Clark

[11] Patent Number: 5,273,961
[45] Date of Patent: Dec. 28, 1993

[54] METHOD OF PROPHYLAXIS OF ACUTE RENAL FAILURE

[75] Inventor: Ross G. Clark, Pacifica, Calif.

[73] Assignee: Genentech, Inc., South San Francisco, Calif.

[21] Appl. No.: 949,594

[22] Filed: Sep. 22, 1992

[51] Int. Cl.⁵ .............................................. A61K 37/36
[52] U.S. Cl. .......................................... 514/8; 514/12; 514/21
[58] Field of Search ................................ 514/8, 12, 21

[56] References Cited

U.S. PATENT DOCUMENTS

| | | | |
|---|---|---|---|
| 5,106,832 | 4/1992 | Froesch et al. | 514/12 |
| 5,126,324 | 6/1992 | Clark | 514/12 |

FOREIGN PATENT DOCUMENTS

WO9211865 7/1992 PCT Int'l Appl. .

OTHER PUBLICATIONS

Gershberg, J. Clin. Endocr. and Metab., 20: 1107–1119 (1960), "Metabolic & Renotropic Effects of hGH in Disease".
Turner et al., in Proc. of 2nd Intl. Symp. on IGF-I/-Somatomedins, Jan. 12–16, 1991, S.F., CA, Spencer, Ed., "Evidence that the Inhibition of Osteoblast Activity . . . ", Elsevier Science Publ. Co (1991) pp. 143–153.
Norman et al., Clin. Science, 78:445–450 (1990).
Han et al., Science, 236: 193–197 (1987).
Gershberg et al., J. Clin. Endocr. & Metab., 17:377–385 (1957).
White et al., J. Clin. Endocr. & Metab., 157:47–51 (1949).
Beck et al., Metab., 13(10 [2]: 1108–1134 (1964).
Hirschberg et al., Kidney Intl., 35: 865–870 (1989).
Haffner et al., Clin. Nephrology, 32(12): 266–269 (1989).
Reiss et al., Kidney Itnl., 37(1): 492 (1990).
Andersson & Jennische, Acta. Physiol. Scand., 132:453–457 (1988).
McConaghey & Dehnel, J. Endocr., 52:587–588 (1972).
Parving et al., Acta Endocr., 89:796–800 (1978).
Corvilain et al., J. Clin. Invest., 41(6):1230–1235 (1962).
Corvilain et al., J. Clin. Invest., 43(8):1608–1612 (1964).
Lajara et al., Am. J. Physiol., 257:F252–F261 (1989).
Koch et al., J. Pediatr., 115:365–371 (1989).
Coimbra et al., Am. J. Physiol., 259:F438–F443 (1990).
Humes et al., J. Clin. Invest., 84:1757–1761 (1989).
Guler et al., Acta Endocr., 121:101–106 (1989).
Hirschberg & Kopple, J. Clin. Invest., 83:326–330 (1989).
Caverzasio et al., Endocr., 127(1):453–459 (1990).
Guler et al, PNAS USA, 86:2868–2872 (1989).
Arnquist et al., Am. J. Physiol., 254:C411–C414 (1988).
Conti et al., Am. J. Physiol., 255:F1214–F1219 (1988).
Pillion et al., Am. J. Physiol., 255:E504–E512 (1988).
Hammerman & Gavin, Am. J. Physiol., 251:E32–E41 (1986).
Rogers & Hammerman, PNAS USA, 86:6363–6366 (1989).
Rogers et al., Am. J. Physiol., 259:F474–F479 (1990).
Han et al., Pediat. Res., 22(3):245–249 (1987).
Fagin & Melmed, Endocr., 120(2):718–724 (1987).
Murphy et al., Endocr., 121(2):684–691 (1987).
D'ercole et al., PNAS USA, 81:935–939 (1984).
Stiles et al., Endocr., 117(6):2397–2401 (1985).
Flysbjerg et al., Modern Concepts of Insulin-Like Growth Factors, Spencer, Ed., Elsevier Publishing, NY, pp. 207–217 (1991).

(List continued on next page.)

Primary Examiner—Howard E. Schain
Assistant Examiner—P. Lynn Touzeau
Attorney, Agent, or Firm—Janet E. Hasak

[57] ABSTRACT

A method is disclosed for the prophylactic treatment of mammals at risk for acute renal failure, whether due to renal ischemia or nephrotoxic damage. This method involves administering to the mammal, before or at the time that the acute renal failure is expected to occur or is occurring, an effective amount of IGF-I. Preferably, the IGF-I is native-sequence, mature human IGF-I.

10 Claims, 21 Drawing Sheets

OTHER PUBLICATIONS

Lemmey et al., Am. J. Physiol., 260:E213–E219 (1991).
Van Bool-Offers et al., Ped. Res., 20(9):825–827 (1986).
Philipps et al., Ped. Res., 23(3):298–305 (1988).
Skottner et al., Endocr., 124(5):2519–2526 (1989).
Scheiwiller et al, Nature, 323:169–171 (1986).
Skottner et al., J. Endocr., 112:123–132 (1987).
Guler et al., PNAS USA, 85:4889–4893 (1988).
Rogers et al., Am. J. Physiol., 259:F474–F479 (1990).
Mulroney & Haramati, 73rd Ann. Mtg., Endocrine Society, 6-19/22-91, p. 141.
Miller et al., Am. J. Physiol., 259:F747–F751 (1990).
Froesch et al, Tem, 1(5):254–260 (1990).
Welbourne & Cronin, Am. J. Physiol., 260:R1036–R1042 (1991).
Hirschberg et al., J. Clin. Inv., 87:1200–1206 (1991).
Quigley & Boum, J. Clin. Invest., 88:368–374 (1991).
Hammerman, Am. J. Physiol., 257:F508–F514 (1989).

METHOD OF PROPHYLAXIS OF ACUTE RENAL FAILURE

BACKGROUND OF THE INVENTION

1. Field of the Invention

This invention relates to a method of preventing or ameliorating acute renal failure in mammals The acute renal failure may be due to reduced renal blood flow or nephrotoxins leading to cell necrosis and reduced kidney function.

2. Description of Related Art

Insulin-like growth factor 1 (IGF-I) is a polypeptide naturally occurring in human body fluids, for example, blood and human cerebral spinal fluid. Most tissues, including the kidney, produce IGF-I together with specific IGF-binding proteins. IGF-I production is under the dominant stimulatory influence of growth hormone (GH), and some of the IGF-I binding proteins are also influenced by GH. See Tanner et al., *Acta Endocrinol.*, 84: 681-696 (1977); Uthne et al., *J. Clin. Endocrinol. Metab.*, 39: 548-554 (1974). IGF-I has been isolated from human serum and produced recombinantly. See, e.g., EP 123,228 and 128,733.

Human growth hormone (hGH) is a single-chain polypeptide consisting of 191 amino acids (molecular weight 21,500). Disulfide bonds link positions 53 and 165 and positions 182 and 189. Niall, *Nature, New Biology*. 230: 90 (1971). hGH is a potent anabolic agent, especially due to retention of nitrogen, phosphorus, potassium, and calcium. Treatment of hypophysectomized rats with GH can restore at least a portion of the growth rate of the rats. Moore et al., *Endocrinology*, 122: 2920.2926 (1988). Among its most striking effects in hypopituitary (GH-deficient) subjects is accelerated linear growth of bone growth plate cartilage resulting in increased stature. Kaplan, *Growth Disorders in Children and Adolescents* (Springfield, Ill.: Charles C. Thomas, 1964).

It has been reported that, especially in women after menopause, GH secretion declines with age. Millard et al., *Neurobiol. Aging*, 229-235 (1990); Takahashi et al., *Neuroendocrinology*, 46: 137-142 (1987). See also Rudman et al., *J. Clin. Invest.*, 67: 1361-1369 (1981) and Blackman, *Endocrinology and Aging*, 16: 981 (1987). Moreover, a report exists that some of the manifestations of aging, including decreased lean body mass, expansion of adipose-tissue mass, and the thinning of the skin, can be reduced by GH treatment three times a week. See, e.g., Rudman et al., *N. Eng. J. Med.*, 323: 1-6 (1990) and the accompanying article in the same journal issue by Dr. Vance (pp. 52-54).

The levels of IGF-I are reported to be reduced by half in 20-month old rats compared to 6-month old rats. Takahashi and Meiters, *Proc. Soc. Exp. Biol. Med.*, 186: 229-233 (1987). See also Florini and Roberts, *J. Gerontol.*, 35: 23-30 (1980); Florini et al., *Mech. Ageing Dev.*, 15: 165-176 (1981); Chatelain et al., *Pediatrie*, 44: 303-308 (1989); Florini et al., *J. Gerontol.*, 40: 2-7 (1985); Hall and Sara, *Clinics in Endocrin. and Metab.*, 13: 91 (1984); Baxter, *Advances in Clinical Chemistry*, 25: 49 (1986); Clemmons and Underwood, *Clinics in Endocrin. and Metab.* 15: 629 (1986); Hintz, *Advances in Pediatrics*, 28: 293 (Year Book Medical Publishers, Inc., 1981); Johanson and Blizzard, *The Johns Hopkins Medical Journal*, 149: 115-117 (1981), the latter five references describing low IGF-I levels in aged men. The Hintz, Clemmons and Underwood, and Baxter references are general reviews on IGF-I.

Furthermore, it was found that among human diploid fibroblasts capable of cycling in aging cultures in vitro, there were few changes in the regulation of the growth fraction by platelet-derived growth factor (PDGF) and epidermal growth factor (EGF), but a greatly increased dependence on IGF-I for regulation of the rate of entry into S phase. Chen and Rabinovitch, *J. Cell. Physiol.*, 144: 18-25 (1990). The authors conclude that the slower growth of the dividing population of cells in aging cultures may be related to a requirement for IGF-I at levels that are greatly above those usually supplied This may be due to overproduction of the IGF-I binding protein, IGFBP-3, and, therefore, a reduction in IGF-I availability to its receptor. Goldstein et al., "Cellular and Molecular Applications to Biology of Aging", AFCR Meeting abstract, Seattle, May 4-5, 1991.

Various biological activities of IGF-I in other than aged mammals have been identified. For example, IGF-I is reported to lower blood glucose levels in humans for use in treating diabetes Guler et al., *N. Engl. J. Med.*, 317: 137-140 (1987); Froesch et al., U.S. Pat. No. 4,988,675. Additionally, IGF-I is reported as useful in treating cardiac disorders (WO 92/11865 published 23 Jul. 1992) and in promoting growth in several metabolic conditions characterized by low IGF-I levels, such as hypophysectomized rats (Skottner et al., *J. Endocr.*, 112: 123-132 [1987]), diabetic rats (Scheiwiller et al., *Nature*, 323: 169-171 [1986]), and dwarf rats (Skottner et al., *Endocrinology*, 124: 2519-2526 [1989]). The anabolic effect of IGF-I in rapidly growing neonatal rats was demonstrated in vivo. Philipps et al., *Pediatric Res.*, 23: 298 (1988). In underfed, stressed, ill, or diseased animals, IGF-I levels are well known to be depressed.

The kidney weight of hypophysectomized rats increases substantially upon prolonged infusions of IGF-I subcutaneously. Guler et al., *Proceedings of the 1st European Congress of Endocrinology*, 103: abstract 12-390 (Copenhagen, 1987); Guler et al., *Proc. Natl. Acad. Sci. USA*. 85: 4889-4893 (1988). The kidneys of Snell dwarf mice and dwarf rats behaved similarly. van Buul-Offers et al., *Pediatr. Res.*, 20: 825-827 (1986); Skottner et al., *Endocrinology*, supra. A truncated IGF-I molecule called des-IGF-I that has the first three amino acids removed from its N-terminus was found to be more potent than IGF-I as a kidney growth factor in GH-deficient rats. Lemmey et al., *Am. J. Physiol.*, 260: E213-E219 (1991).

There is a long history of studies showing that the administration of GH to humans and animals increases glomerular filtration rate, renal plasma flow, proximal tubular phosphate reabsorption, and proximal tubular gluceoneogenesis. Corvilain and Abramow, *J. Clin. Invest.*, 41: 1230-1235 (1962); Corvilain and Abramow, *J. Clin. Invest.*, 43: 1608-1612 (1964). Besides these effects on kidney function, GH excess has also been reported to cause glomeruli and proximal tubules to hypertrophy (Gershberg et al., *J. Clin. Endocrinol. Metab.*, 17: 377-385 [1957]). However, it was also recognized that some of these effects of GH were not direct, as in humans kidney function was unchanged by short-term GH infusions. Parving et al., *Acta Endocrinol.*, 89: 796-800 [1978].

The GH-IGF axis is implicated in normal tissue growth and anabolic activity throughout the body. The actions of GH are believed to be largely mediated by the IGFs, which were originally termed "somatomedins," or mediators of growth. IGF-I levels increase in contralateral kidneys 1-2 days following unilateral nephrectomy, experimental diabetes, and potassium depletion. Flyvbjerg et al., "Kidney IGF-I Accumulation Occurs in Four Different Conditions with Rapid Initial Kidney Growth in Rats," *Modern Concepts of Insulin-Like Growth Factors*, EM Spencer, eds., Elsevier Publishing, N.Y., pp. 207-217 (1991); Stiles et al., *Endocrinology*, 117: 2397-2401 (1985). It was found that GH stimulates IGF-I gene expression in an isolated rat renal collecting duct. Rogers et al., *J. Amer. Phys.*, F474-F479 (1990). GH can correct a striking acidification defect in hypophysectomized rat kidneys in a dose-dependent manner. Welbourne and Cronin, *Amer. J. Phys.*, R1036-R1042 (1991).

While some of the effects previously seen with GH were subsequently seen when IGF-I was administered to animals and humans (Guler et al., *Proc. Natl. Acad. Sci. USA*, 85: 4889-4893 [1988]), the IGFs are not necessarily regulated by GH. Different results of the effects of GH and IGF-I on rabbit proximal convoluted tubule transport were seen by Quigley and Baum, *J. Clin. Invest.*, 88: 368-374 (1991). In their hands, while GH had no effect on phosphate transport, IGF-I stimulated directly phosphate transport in the rabbit proximal convoluted tubule.

There were concurrent reports that the kidney produced IGFs in response to GH administration, and that IGF-I is highly concentrated in renal tissue McConaghey and Dehnel, *J. Endocrinol.*, 52: 587-588 (1972); D'Ercole et al., *Proc. Natl Acad. Sci. USA* 81: 935-939 (1984). These observations were expanded subsequently to show a steady-state level of IGF-I mRNA in the kidney even in the absence of GH (Murphy et al., *Endocrinology*, 121: 684-691 [1987]) and the localization by immunohistochemistry of IGF-I peptide to kidney collecting ducts. Andersson and Jennische, *Acta Physiol. Scand.*, 132: 453-457 (1988). Also, IGF-I mRNA has been identified in the collecting duct of rat kidneys (Fagin and Melmed, *Endocrinol.*, 120: 718-723 [1987]) and in the human fetus. Han et al., *Science Wash. EDC*, 236: 193-198 (1987); Han et al., *Pediatrics Res.*, 22: 245-247 (1987). Further, the efficacy of IGF-I on kidney growth was not reduced by concurrent GH administration. U.S. Pat. No. 5,126,324 issued Jun. 30, 1992.

In the kidney IGF-I mRNA is produced both autonomously and by GH binding to receptors in the collecting ducts, which increases IGF-I mRNA. The IGF-I produced then enters the extracellular space to interact in a paracrine fashion with IGF-I receptors in the proximal tubule. GH was found to stimulate IGF-I gene expression in an isolated rat renal collecting duct. Rogers et al., *Am. J. Physiol.*, 259: F474-F479 [1990]. Renal tissue is very responsive to IGF-I due to high concentrations of IGF-I receptors on membranes of the renal cells. Hammerman, *Am J. Physiol.*, 257: F503-F514 (1989); Rogers and Hammerman, *Proc. Natl. Acad. Sci. USA*. 86: 6363-6366 (1989); Hammerman and Gavin, *Am. J. Physiol.*, 251: E32-E41 (1986): Pillion et al., *Am. J. Physiol.*, 255: E504-E512 (1988): Hammerman and Rogers, *Am. J. Physiol.*, 253: F841-F847 (1987). IGF-I receptors are also located in the arterial smooth muscle, vascular endothelium, and basolateral membrane. Conti et al., *Am J. Physiol.*, 255: F1214-F1219 (1988); Arnqvist et al., *Am J. Physiol.*, 254: C411-C414 (1988).

Elevated circulating GH is associated with increased renal plasma flow and glomerular renal flow. Indeed, measures of renal hemodynamics rise within several hours after a single injection of GH, at about the same time that serum IGF-I concentrations increase. These findings suggested that IGF-I may increase renal plasma flow and glomerular filtration rate. In fact, IGF-I was found to increase glomerular filtration and renal plasma flow (Guler et al., *Proc. Natl. Acad. Sci. USA*, 86: 2868-2872 [1989]), and to stimulate renal phosphate transport and plasma 1,25-dihydroxyvitamin $D_3$. Caverzacio et al., *Endocrinol.*, 127: 453-459 [1990]. Further, a short term infusion of IGF-I alone into rats fasted for 60-72 hours was found to increase glomerular filtration rate (Hirschberg and Koppel, *J. Clin. Invest.*, 83: 326-330 [1989]; see also Hirschberg et al., *J. Clin. Invest.*, 87: 1200-1206 [1991]), and administration of IGF-I to humans was found to elevate glomerular filtration rate and renal plasma flow. Guler et al., *Acta Endocrinol.*, 121: 101-106 (1989); Froesch et al., *Trends in Endocrinology and Metabolism*, p. 254-260 Vol. 1, Issue 5 (Elsevier Science Pub. Co., 1990). See also U.S. Pat. No. 5,106,832 issued 21 Apr. 1992.

In addition, EGF has been shown to accelerate the regeneration of renal repair in post-ischemic acute renal failure (Humes et al., *J. Clin. Invest.*, 84: 1757-1761 [1989]; Norman et al., *Clin. Sci.*, 78: 445-450 [1990]), and after damage with the nephrotoxin mercuric chloride. Coimbra et al., *Am. J. Physiol.*, 259: F438 (1990). In addition, another growth factor, transforming growth factor-α (TGF-α) also has been reported to accelerate renal repair and recovery from ischemic injury to the kidney. Reiss et al., *Kidney Internat.*, 37: 492 (1990).

Because administration of GH was found to increase glomerular filtration rate and renal plasma flow (Haffner et al., *Clin. Nechrol.*, 32: 266-269 [1989]; Hirschberg et al., *Kidney Int.*, 35: 865-870 [1989]), it has been suggested that this hormone could be used as a pharmacological agent to enhance renal function in the setting of chronic renal failure Gershberg, *J. Clin. Endocrinol. Metab.*, 20: 1107-1119 (1960); White et al., *Am. J. Physiol.*, 157: 47-51 (1949). However, in contrast to findings in the backdrop of normal renal function, administration of GH to human adults (Beck et al., *Metabolism*, 13: 1108-1134 [1964]; Haffner, supra) or children (Koch et al., *J. Pediatr.*, 115: 365-371 [1989]) with chronic renal failure does not increase glomerular filtration rate. These studies employed subjects with chronic renal failure of varying severity and of many etiologies.

The acute role of IGF-I in the growth or repair of the kidney is more controversial. There are data showing that IGF-I protein is increased in kidneys undergoing hypertrophy due to GH treatment (D'Ercole et al., supra) or hypertrophy in the remaining kidney following unilateral nephrectomy (Stiles et al., supra), or following ischemic injury to the kidney (Andersson and Jennische, supra). Additionally, as of 1991 the role of IGF-I in renal compensatory hypertrophy was described as controversial. See Mulroney and Haramati, *73rd Annual Meeting, The Endocrine Society*, Jun. 19-22, 1991, page 141 of Programs and Abstracts book, abstract 444. However, as IGF-I has many roles in the kidney, the elevation in tissue IGF-I content in these circumstances is not necessarily indicative of a role in the growth response of the kidney.

There is a major difference between the locality of IGF-I mRNA and IGF-I receptor mRNA. Message for IGF-I is found chiefly in collecting ducts "downstream" from the bulk of kidney IGF-I receptors, which are found mainly in the proximal tubules and are lacking in collecting ducts. Lajara et al., *Am. J. Physiol.*, 257:

F252-F261 (1989). This different distribution of receptors and ligand is unusual in that IGF-I receptors are found in the kidney cortex while IGF-I is found in the kidney medulla. It is possible that local renal IGF-I peptide has little activity in the kidney and that the IGF-I receptors in the tubules chiefly respond to endocrine IGF-I derived from the general circulation. The fundamental significance of changes in renal IGF-I (mRNA or peptide concentration), for example following renal damage, is therefore questionable. Also see Miller and Hammerman, *Am. J. Physiol.*, F747-F751 (1990) and Martin et al., *Proc. 2nd Int. IGF Symposium*, p. 142 (1991).

Acute renal failure (ARF) complicates the course of nearly 5% of all hospitalized patients and 20% of intensive care unit patients. In 1% of all admissions renal failure is severe, increasing the overall risk of death six-fold. ARF is usually due to reduced renal blood flow caused by destruction of the proximal tubule or nephrotoxins leading to cell necrosis. This is followed by retention of nitrogenous products, fluids, and electrolytes and a state of accelerated catabolism. If the ARF is severe and prolonged, death occurs unless hemodialysis therapy is instituted. Current therapy includes early diagnosis and supportive care including fluid balance, electrolyte homeostasis, treatment of complicating medical problems, dialysis for any involved nephrotoxins, and careful monitoring. During this latter phase, which may last weeks, the patient is at high risk. There is a need in the art for a drug that will prevent ARF from occurring in the first instance or at least ameliorate its effects.

It is therefore an object of the present invention to provide a drug that is useful in preventing or ameliorating ARF in mammals that are at risk of suffering from ARF.

It is one specific object to prevent or ameliorate, most commonly, acute tubular necrosis leading to oliguria and azotermia, typically from an ischemic renal injury. Recovery from such moderate-severe injury typically requires in-patient dialysis, takes 4-6 weeks, and is associated with significant mortality.

It is another specific object to eliminate or decrease the need for dialysis in patients with ARF.

It is a further specific object to prevent or ameliorate nonoliguric renal failure.

These objects will be apparent to those of ordinary skill in the art.

SUMMARY OF THE INVENTION

Accordingly, the present invention provides a method for prophylaxis of ARF in a mammal at risk for ARF comprising administering to the mammal an effective amount of IGF-I before or at the time that ARF is expected to occur or is occurring.

If IGF-I is given prior to or when damage to the kidney is expected to occur or is occurring, whether due to ischemia or nepthrotoxins, ARF can be at least ameliorated, if not prevented.

DESCRIPTION OF THE PREFERRED EMBODIMENTS

A. Definitions

Figure 1:
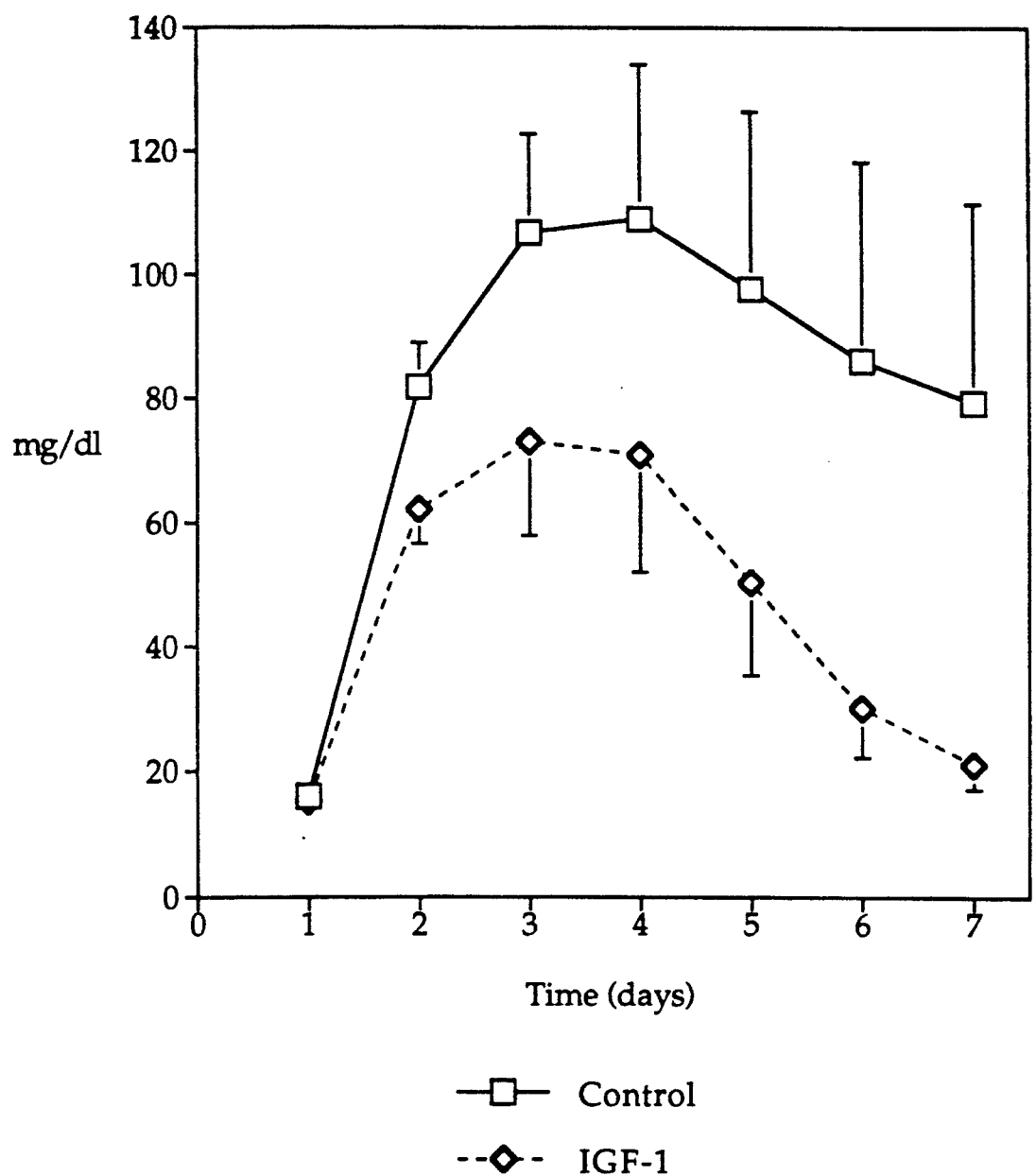
FIG. 1 is a graph of blood urea nitrogen levels in rabbit renal ischemia and reperfusion for the control (solid squares) and IGF-I-treated rabbits (open squares) over seven days.

As used herein, "acute renal failure" or "ARF" refers to a condition caused by reduced renal blood flow (ischemic renal injury) due to destruction of the proximal tubule of the kidney or by nephrotoxins leading to cell necrosis. This covers moderate to severe ARF, including acute tubular necrosis leading to oliguria and azotermia, and nonoliguric renal failure. It is characterized by such symptoms as retention of nitrogenous products, fluids, and electrolytes and a state of accelerated catabolism. If the ARF is severe, death occurs unless hemodialysis therapy is instituted.

ARF causes kidney damage that is characterized by acute tubular edema, necrosis, or interstitial or tubular edema after ischemic injury thereto. The renal ischemia may be caused by any means, including decreased blood pressure, particularly prolonged hypotension, cardiac or aortic bypass surgery, or renal transplantation. In addition, it may have been induced, for example, by physical damage or wounding of the kidney. Thus, the IGF-I can be used to maintain kidney integrity before or during renal transplantation.

Examples of nephrotoxins leading to cell necrosis include cyclosporine, heavy metal poisoning, intravenous contrast dye administration, antibiotics such as aminoglycosides, e.g., tobramycin, gentamycin, amikacin, and streptomycin, and antifungal agents such as amphotericin.

"Prophylaxis" of ARF refers to prevention, or at least amelioration, of ARF.

Mammals "at risk" for ARF are those mammals, including mammals of economic importance such as bovine, ovine, and porcine animals, as well as humans, the latter being preferred, that are prone to exhibit ARF from operations or transplants to be performed or illnesses likely to be incurred.

As used herein, "IGF-I" refers to insulin-like growth factor from any species, including bovine, ovine, porcine, equine, avian, and preferably human, in native-sequence or in variant form, and from any source, whether natural, synthetic, or recombinant. Preferred herein for animal use is that form of IGF-I from the particular species being treated, such as porcine IGF-I to treat pigs, ovine IGF-I to treat sheep, bovine IGF-I to treat cattle, etc. Preferred herein for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations. Also preferred for use is IGF-I that has a specific activity greater than about 14,000 units/mg as determined by radioreceptor assay using placenta membranes, such as that available from KabiGen AB, Stockholm, Sweden.

The most preferred IGF-I variants are those described in U.S. Pat. No. 5,077,276 issued Dec. 31, 1991, in PCT WO 87/01038 published Feb. 26, 1987 and in PCT WO 89/05822 published Jun. 29, 1989, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-I, des(1-3) IGF-I, or des-IGF-I).

B. Modes for Carrying Out the Invention

Prophylaxis is accomplished by treatment with IGF-I before or at the time that damage to the kidney (ARF) is expected to occur or is occurring, i.e., prior to ongoing damage up to and including the period during which the damage is expected or is ongoing.

For example, the treatment with IGF-I to prevent or ameliorate kidney damage or to prevent rejection of a transplanted kidney is initiated before or while kidney damage is expected to occur or is occurring, i.e., before or at the time of elective surgery for coronary or thoracic surgery, before or during nephrotoxin administration, or before or during introduction of a kidney transplant.

If the treatment is done before kidney damage is expected to occur or is occurring, it is preferably done from about 48 hours to about 0.5 hour, before the damage is expected or is occurring. Optionally, the administration of IGF-I is suitably continued after ARF is expected to occur or is occurring. Clinical symptoms of kidney damage, which generally do not arise immediately during damage, but may take up to 24 hours or longer to appear, include increased blood urea nitrogen or creatinine levels or decreased organic ion transport.

For the various purposes of this invention, the IGF-I is directly administered to the mammal by any suitable technique, including parenterally, and can be administered locally or systemically. The specific route of administration will depend, e.g., on the medical history of the patient, including any perceived or anticipated side effects using IGF-I. Examples of parenteral administration include subcutaneous, intramuscular, intravenous, intraarterial, and intraperitoneal administration.

Preferably, the administration is by continuous infusion (using, e.g., minipumps such as osmotic pumps and a subcutanous route), or by a single injection or multiple (e.g., 2-4) injections using, e.g., intravenous or subcutaneous means before or at the time of initiation of the insult likely to lead to kidney damage. Preferably, the administration is subcutaneous for IGF-I. The administration may also be as a single bolus or by slow-release depot formulation.

In addition, the IGF-I is suitably administered together with any one or more of its binding proteins, for example, those currently known, i.e., IGFBP-1, IGFBP 2, IGFBP-3, IGFBP-4, IGFBP-5, or IGFBP-6. The IGF-I is also suitably coupled to a receptor or antibody or antibody fragment for administration. The preferred binding protein for IGF-I herein is IGFBP-3, which is described in WO 89/09268 published Oct. 5, 1989 and by Martin and Baxter, *J. Biol. Chem.*, 261: 8754–8760 (1986). This glycosylated IGFBP-3 protein is an acid-stable component of about 53 Kd on a non-reducing SDS-PAGE gel of a 125–150 Kd glycoprotein complex found in human plasma that carries most of the endogenous IGFs and is also regulated by GH.

The administration of the IGF binding protein with IGF-I is suitably accomplished by the method described in copending U.S. Ser. No. 07/654,436 filed 12 Feb. 1991, the disclosure of which is incorporated herein by reference. Briefly, the IGF-I and IGFBP are administered in effective amounts by subcutaneous bolus injection in a molar ratio of from about 0.5:1 to about 3:1, preferably about 1:1.

The IGF-I composition to be used in the therapy will be formulated and dosed in a fashion consistent with good medical practice, taking into account the clinical condition of the individual patient (especially the side effects of treatment with IGF-I alone), the site of delivery of the IGF-I composition, the method of administration, the scheduling of administration, and other factors known to practitioners. The "effective amount" of IGF-I for purposes herein is thus determined by such considerations.

As a general proposition, the total pharmaceutically effective amount of the IGF-I administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the IGF-I is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed. The key factor in selecting an appropriate dose is the result obtained, as measured by regeneration of the proximal tubular epithelium, prevention of accelerated catabolism, prevention of excess accumulated nitrogenous products, fluids, and electrolytes, etc.

The IGF-I is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman et al., *Biocolymers*, 22, 547–556 [1983]), poly(2-hydroxyethyl methacrylate) (Langer et al., *J. Biomed. Mater. Res.*, 15: 167–277 [1981], and Langer, *Chem. Tech.*, 12: 98–105 [1982]), ethylene vinyl acetate (Langer et al., supra) or poly-D-(—)-3-hydroxybutyric acid (EP 133,988). Sustained-release IGF-I compositions also include liposomally entrapped IGF-I. Liposomes containing IGF-I are prepared by methods known per se: DE 3,218,121; Epstein et al., *Proc. Natl. Acad. Sci. U.S.A.*, 82: 3688–3692 (1985); Hwang et al., *Proc. Natl. Acad. Sci. U.S.A.*, 77: 4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (about 200.800 Angstroms) unilamellar type in which the lipid content is greater than about 30 mol. percent cholesterol, the selected proportion being adjusted for the optimal IGF-I therapy.

For parenteral administration, in one embodiment, the IGF-I is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IGF-I uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The IGF-I is typically formulated in such vehicles at a concentration of about 0.1 mg/ml to 100 mg/ml, preferably 1–10 mg/ml, at a pH of about 3 to 8. Full-length IGF-I is generally stable at a pH of no more than about 6; des(1-3) IGF-I is stable at about 3.2 to 5. It will be understood that use of certain of the foregoing excipients, carriers, or stabilizers will result in the formation of IGF-I salts.

In addition, the IGF-I, preferably the full-length IGF-I, is suitably formulated in an acceptable carrier vehicle to form a pharmaceutical composition, preferably one that does not contain cells. In one embodiment, the buffer used for formulation will depend on whether the composition will be employed immediately upon mixing or stored for later use. If employed immediately, the full-length IGF-I can be formulated in mannitol, glycine, and phosphate, pH 7.4. If this mixture is to be stored, it is formulated in a buffer at a pH of about 6, such as citrate, with a surfactant that increases the solubility of the IGF-I at this pH, such as 0.1% polysorbate 20 or poloxamer 188. The final preparation may be a stable liquid or lyophilized solid.

IGF-I to be used for therapeutic administration must be sterile. Sterility is readily accomplished by filtration through sterile filtration membranes (e.g., 0.2 micron membranes). Therapeutic IGF-I compositions generally are placed into a container having a sterile access port, for example, an intravenous solution bag or vial having a stopper pierceable by a hypodermic injection needle.

IGF-I ordinarily will be stored in unit or multi-dose containers, for example, sealed ampoules or vials, as an aqueous solution, or as a lyophilized formulation for reconstitution. As an example of a lyophilized formulation, 10-ml vials are filled with 5 ml of sterile-filtered 1% (w/v) aqueous IGF-I solution, and the resulting mixture is lyophilized. The infusion solution is prepared by reconstituting the lyophilized IGF-I using bacteriostatic Water-for-Injection.

GH may also be administered to the mammal being treated with IGF-I in accordance with this invention. The GH may be administered at any suitable time for this purpose. Thus, GH is suitably administered before or at the time that the ARF is expected to occur or is occurring, and it is also suitably administered or continued to be administered after ARF is expected to occur or is occurring.

If GH is employed, it may be administered separately from the IGF-I or combined with the IGF-I, in a dose and using a suitable administration as is used for IGF-I above, typically at least 0.1 mg/kg/day. It is noted that hGH is stable at a higher pH than IGF-I, e.g., 7.4–7.8.

Also GH is suitably administered together with one or more of its binding proteins. A well characterized such binding protein is the high-affinity growth hormone binding protein (GHBP) constituting the extracellular domain of the GH receptor that circulates in blood and functions as a GHBP in several species (Ymer and Herington, *Mol. Cell. Endocrino.*, 41: 153 [1985]; Smith and Talamantes, *Endocrinology*, 123: 1489–1494 [1988]; Emtner and Roos, *Acta Endocrinologica (Copenh.)*, 122: 296–302 [1990]), including man. Baumann et al., *J. Clin. Endocrinol. Metab.*, 62: 134–141 (1986); EP 366,710 published 9 May 1990; Herington et al., *J. Clin. Invest.*, 77: 1817–1823 (1986); Leung et al., *Nature*, 330: 537–543 (1987). A second BP with lower affinity for GH has also been described that appears to be structurally unrelated to the GH receptor. Baumann and Shaw, *J. Clin. Endocrinol. Metab.*, 70: 680–686 (1990).

The doses of both GH and IGF-I can be less if used together than if IGF-I is administered alone. It is noted that practitioners devising doses of both IGF-I and GH should take into account the known side effects of treatment with these hormones. For hGH the side effects include sodium retention and expansion of extracellular volume (Ikkos et al., *Acta Endocrinol.* (Copenhagen), 32: 341–361 [1959]; Biglieri et al., *J. Clin. Endocrinol. Metab.*, 21: 361–370 [1961]), as well as hyperinsulinemia and hyperglycemia. The major apparent side effect of IGF-I is hypoglycemia. Guler et al., *Proc. Natl. Acad. Sci. USA* (1989), supra. Indeed, the combination of IGF-I and GH may lead to a reduction in the unwanted side effects of both agents (e.g., hypoglycemia for IGF-I and hyperinsulinism for GH) and to a restoration of GH secretion that is suppressed by IGF-I.

In addition, the IGF-I is suitably administered in combination 10 with other therapies for preventing or ameliorating further ischemic or nephrotoxic injury. Substances useful for this purpose include superoxide dismutase and antagonists (e.g., antibodies) to VLA-4, LFA-1, Mac-1, p150,95, EGF, TGF-α, etc. These agents may be administered at the same time as, before, or after the administration of IGF-I and can be administered by the same or a different administration route than the IGF-I is administered.

The invention will be more fully understood by reference to the following examples. They should not, however, be construed as limiting the scope of the invention. All literature and patent citations are expressly incorporated by reference.

EXAMPLE I

First Study on Treatment of Rabbits

Introduction

To monitor the progress in animals of ARF and their response over time to excipient or IGF-I or des-IGF-I, BUN and creatinine levels in serum were measured. Creatinine, the metabolic product of muscle activity, remains relatively constant in plasma levels, assuming measures are not made after maximal exertion. Urea nitrogen measures are less reliable, being affected by metabolic state, diet, hydration, and other factors. However, clearance of both urea nitrogen and creatinine markedly decreases during renal failure and acute renal damage, regardless of metabolic or physiologic state. These two constituents are accepted indicators of renal function, and their blood concentrations reflect those of other injurious compounds elevated in nephropathies. Creatinine is filtered by the kidney but not secreted or reabsorbed; urea nitrogen is filtered and reabsorbed passively. Together, they gauge renal function, and are key laboratory parameters in monitoring renal failure.

Protocol

Recombinant human IGF-I [available commercially from KabiGen AB, Stockholm, Sweden (specific activity > 14,000 U/mg by radioreceptor assay using placental membranes) or available for clinical investigations from Genentech, Inc., South San Francisco] was employed in all the IGF-I experiments detailed in the examples. For this example, the IGF-I was dissolved at 5 mg/ml in 10 mM citrate buffer and 126 mM NaCl, pH 6.0.

Male New Zealand White rabbits weighing 2.5 to 3.0 kg were used throughout the study. After a pre-medication of 0.1 ml Hypnorm TM brand anesthesia (1.0 mg Fluanisone TM tumor necrosis factor-alpha and 0.315 mg Fentanyl TM /ml solution) intravenously (i.v.), a 1-ml blood sample was taken from an ear artery. The blood was immediately placed in Vacutainer TM serum separation tubes. The animals were then fully anesthetized with 0.68 ml/kg Hypnorm TM intramuscularly (i.m.). Once tethered to a board, the animals were prepared for sterile surgery by clipping of abdominal fur, cleaning of the surgical field with iodine solution, delipidation with alcohol and secondary cleaning with iodine. Under sterile conditions, a laparotomy was performed. Using saline-soaked gauze, the intestines were displaced to expose the left kidney. The left renal artery was dissected free and clamped with a Serrefin TM clip (Baby Dieffenbach Serrefin; Harvard Apparatus; Cat. No. 52-3241 or 52-3258). The procedure was then repeated for the right renal artery. After occlusion of both renal arteries, two Alzet TM osmotic pumps (Alza Corporation, Palo Alto, Calif., Model 2ML-1 of 2144 μl fill) containing 5 mg/ml of recombinant human IGF-I were placed on either side of the abdominal cavity. These pumps were primed so that they operated immediately upon placement. Each pump delivered 11.75 μl/hours.

So each animal received 2.82 mg/day/animal or approximately 1 mg/kg/day. The laparotomy wound was covered with saline-soaked gauze and sterile towels. During the two-hour ischemia period anesthesia was maintained with supplemental i.v. doses of Hypnorm TM (0.2-0.5 ml).

After two hours of ischemia the clips were removed. The laparotomy closed using 4.0 Prolene TM suture for the abdominal muscle and 2.0 Prolene TM for the skin. The animals were then allowed to recover in a water-heated intensive care incubator until a sternal posture was resumed. The animals were then housed individually with free access to standard laboratory chow and tap water. Surgery was carried out on a total of 12 animals on two days: six animals (2 controls and 4 treated) on one day and 6 animals (3 controls and 3 treated) on a day 11 days later.

Blood Samples

After 24 hours and subsequently every 24 hours thereafter for a total of 6 days, 1-ml samples of blood were taken from the ear artery or vein. The samples were clotted in serum separation tubes and centrifuged at 10° C. to separate serum. The serum was removed and placed in Epindorf tubes and stored at −20° C. to await analysis. This period was usually 24-36 hours (rarely more than 48 hours). The samples were then thawed and BUN, serum creatinine, and blood glucose levels were measured on a Monarch centrifugal analyzer, model 76.

Statistical Analysis

Statistical differences between groups was assessed using a two-way analysis of variance (ANOVA) for repeated measures followed by a least significant difference (LSD) test to identify significant differences between individual time points.

Results

Out of five control animals all survived for seven days; one out of seven treated animals died on day 4 (3 days after surgery). This animal was subsequently eliminated from the study.

BUN

In control animals BUN prior to surgery was 16±0.89 mg/dL; this rose to a maximum of 109±25 mg/dL on day 4, a 5.81 fold increase. See Table 1.

TABLE 1

| \multicolumn{4}{c}{Values for BUN in Saline-Treated Control Animals} |
| Day No. | Mean | Standard Deviation | SEM |
| --- | --- | --- | --- |
| 1 | 16.00 | 2.00 | 0.89 |
| 2 | 81.80 | 15.97 | 7.14 |
| 3 | 106.80 | 35.60 | 15.92 |
| 4 | 109.00 | 56.03 | 25.06 |
| 5 | 97.60 | 64.43 | 28.82 |
| 6 | 86.00 | 71.83 | 32.12 |
| 7 | 79.20 | 72.12 | 32.25 |

Animals chosen at random and treated with IGF-I had similar pre-surgery levels of BUN to those chosen as controls. The maximum increase in BUN levels in these animals was somewhat smaller (73±15.6 mg/dL) at day 3 (Table 2 and FIG. 1). Additionally, the BUN levels in these animals had returned almost to control values by day 7. See Table 2.

TABLE 2

| Values for BUN in IGF-I-treated Animals | | | |
| --- | --- | --- | --- |
| Day No. | Mean | Standard Deviation | SEM |
| 1 | 15.17 | 2.32 | 0.95 |
| 2 | 62.17 | 13.47 | 5.50 |
| 3 | 73.00 | 36.90 | 15.06 |
| 4 | 70.83 | 46.08 | 18.81 |
| 5 | 50.33 | 36.72 | 14.99 |
| 6 | 30.00 | 19.18 | 7.83 |
| 7 | 21.00 | 9.72 | 3.97 |

The concentration of urea nitrogen in the blood of the treated animals was significantly lower at day 6 and day 7. See FIG. 1.

Serum Creatinine

Figure 2:
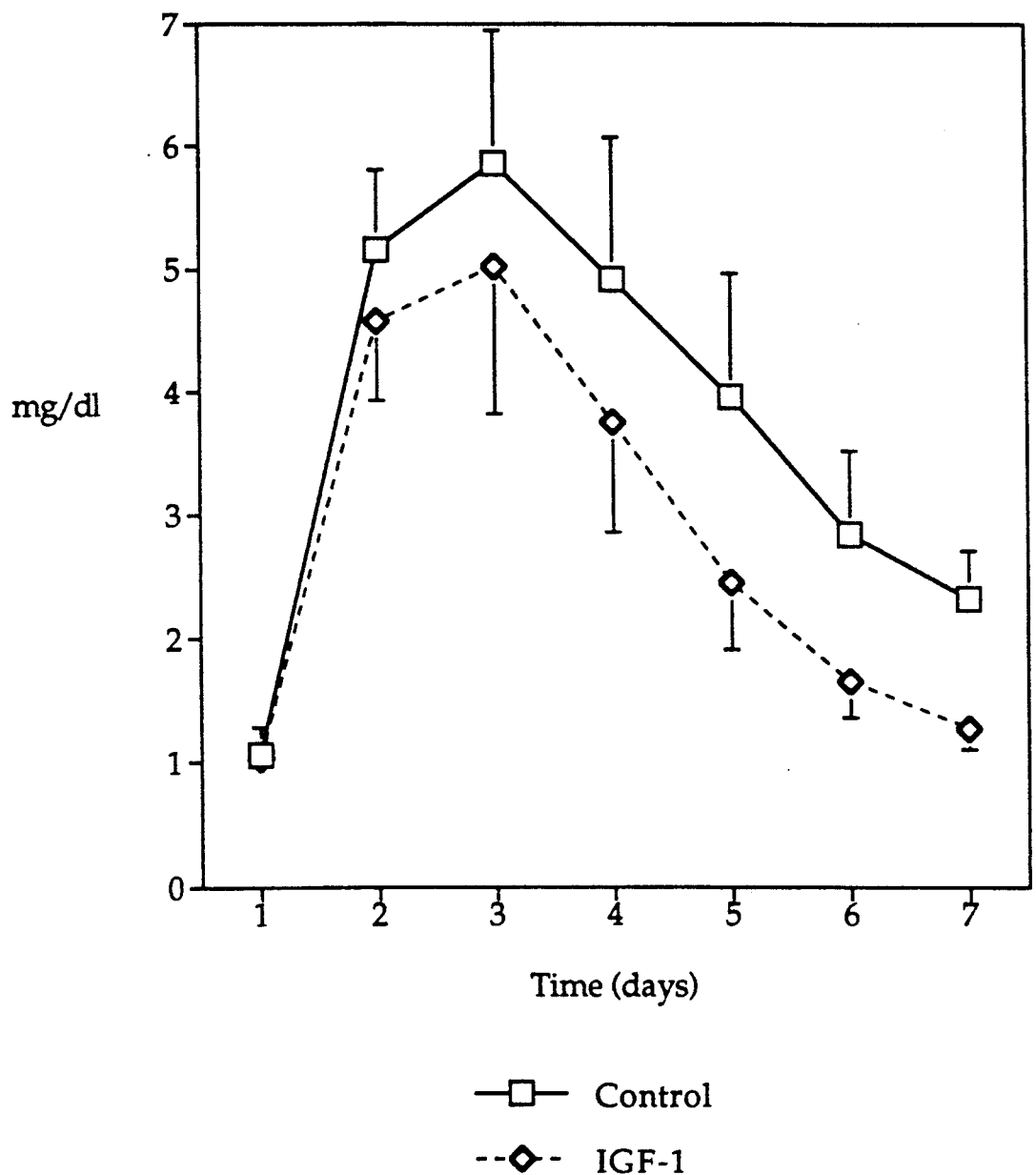
FIG. 2 is a graph of serum creatinine levels in rabbit renal ischemia and reperfusion for the control (solid squares) and IGF-I-treated rabbits (solid diamonds) over seven days.

There were no significant differences in the serum creatinine levels of control or treated animals (Tables 3 and 4; FIG. 2), although the values on days 5 and 6 and 7 in treated animals were half those in untreated animals.

TABLE 3

| Values for Serum Creatinine in Saline-Treated Control Animals | | | |
| --- | --- | --- | --- |
| Day No. | Mean | Standard Deviation | SEM |
| 1 | 1.06 | 0.48 | 0.22 |
| 2 | 5.16 | 1.46 | 0.65 |
| 3 | 5.86 | 2.43 | 1.09 |
| 4 | 4.92 | 2.58 | 1.15 |
| 5 | 3.96 | 2.25 | 1.01 |
| 6 | 2.84 | 1.51 | 0.68 |
| 7 | 2.32 | 0.87 | 0.39 |

TABLE 4

| Values for Serum Creatinine in IGF-I-Treated Animals | | | |
| --- | --- | --- | --- |
| Day No. | Mean | Standard Deviation | SEM |
| 1 | 1.03 | 0.14 | 0.06 |
| 2 | 4.58 | 1.60 | 0.65 |
| 3 | 5.02 | 2.94 | 1.20 |
| 4 | 3.75 | 2.17 | 0.89 |
| 5 | 2.45 | 1.31 | 0.54 |
| 6 | 1.65 | 0.72 | 0.29 |
| 7 | 1.27 | 0.42 | 0.17 |

Blood Glucose

Blood glucose levels in both groups dropped by approximately 60 mg/dL on the first day after surgery and plateaued at 130-160 mg/dL for both groups for the remainder of the experimental period. No statistical difference was observed between the two groups (Tables 5 and 6).

TABLE 5

| Blood Glucose Levels in Control Animals | | | |
| --- | --- | --- | --- |
| Day No. | Mean | Standard Deviation | SEM |
| 1 | 182.40 | 22.23 | 9.94 |
| 2 | 119.60 | 13.24 | 5.92 |
| 3 | 142.60 | 21.20 | 9.48 |
| 4 | 155.80 | 22.61 | 10.11 |
| 5 | 148.20 | 34.22 | 15.30 |
| 6 | 156.60 | 32.30 | 14.45 |
| 7 | 165.40 | 32.75 | 14.64 |

TABLE 6

| Blood Glucose Levels in IGF-I-Treated Animals | | | |
| --- | --- | --- | --- |
| Day No. | Mean | Standard Deviation | SEM |
| 1 | 181.00 | 33.39 | 13.63 |
| 2 | 124.83 | 20.44 | 8.34 |

TABLE 6-continued

Blood Glucose Levels in IGF-I-Treated Animals

| Day No. | Mean | Standard Deviation | SEM |
|---|---|---|---|
| 3 | 134.00 | 10.37 | 4.23 |
| 4 | 140.83 | 7.91 | 3.23 |
| 5 | 134.33 | 12.56 | 5.13 |
| 6 | 130.50 | 14.72 | 6.01 |
| 7 | 146.00 | 21.89 | 8.94 |

Conclusion

The administration of IGF-I at the time of induction of renal ischemia significantly reduced the levels of BUN and appeared to reduce serum creatinine in rabbits that had been subjected to two hours of renal ischemia followed by six days of reperfusion. The BUN levels in the treated animals showed a more rapid and complete return to pre-surgery values and were significantly lower than the saline-treated controls by day 6. This shows that IGF-I is capable of preventing or at least ameliorating renal damage in a mammal at risk for ARF.

EXAMPLE II

Second Study on Treatment of Rabbits

Introduction

This study used more rabbits, and not only were BUN and creatinine levels measured, but kidney function was further assessed by studying the uptake of organic ions by the proximal tubular cells to assess in vitro renal cellular function. Cation transport by renal tubules has been demonstrated in many animals, including rabbits and humans (Besseghir et al., *Am. J. Physiol.*, 241: F308–F314 [1981]; Rennick et al., *Am. J. Physiol.*, 232: F443–F447 [1977]), and plays an essential role in excretion of endogenous and synthetic cations.

To enter the tubular lumen, molecules must cross both the basolateral and brush border membranes (BLM and BBM, respectively). Entry of cations across the BLM appears driven by electrical gradient; transport across the BBM is an electroneutral counterexchange between cation and proton. Dantzler et al., *Am. J. Physiol.*, 256: F290–F297 (1989); Montrose-Rafizadeh et al., *Am. J. Physiol.* 257: F243–F251 (1989). With the in vitro design described below, concentrated cation most likely enters the BLM similarly, but reverse entry across the BBM countertransporters secondary to the concentration gradient is also possible. Anion secretion has been postulated to be a combination of BLM active transport with subsequent diffusion into luminal fluid. Tune et al., *Am. J. Physiol.*, 217: 1057–1063 (1969).

In the studies herein, these transporters were studied in vitro with $^{14}$C-TEA (tetraethylammonium) and $^3$H-PAH. TEA is not broken down intracellularly and thus serves as a good measure of uptake capacity. PAH is metabolized, but only slowly. The cortical slice technique, first used in 1930, has been in wide use for a decade. Several variables must be controlled: tissue thickness, media oxygen content, media ion levels, and agitation during the incubation period. In this example, these variables were accounted for, as described below.

Organ weights and body weights by group, as well as serum urea nitrogen and creatinine levels, are recorded as group average±SEM. Data for cortical slice results are recorded as average of slice/medium for a given time and rabbit. These ratios were then collected by group to get average and SEM for each group. P values for one and two factor ANOVA are reported. Often, the variables for 2-factor ANOVA are day of treatment and value of particular measurement against the treatment group. In cases where day is used, Day 0 is not included, as it is a control measurement, and calculations sometimes exclude the first day (since the drug's action presumably is more obvious in subsequent days) and the last day of treatment (since those rabbits who survived to the last day had typically recovered to near normal state, and those that died of renal failure were no longer in the study).

The effects of IGF-I and the truncated molecule, des-IGF-I, on kidney function following renal damage induced by renal ischemia were studied in this example. It is shown below that both IGF-I and des-IGF-I are effective agents in regenerating the kidney after ischemic injury.

Protocol

Preparation of the Animal Model

Male New Zealand White rabbits (2–3 kg) were acclimated to the animal care facility for several days and entered into the study. They were housed in a room controlled for temperature and lighting and fed rabbit nuts and water ad libitum.

Experimental Groups

Animals were randomly allocated to one of six treatment groups: renal arterial occlusion plus IGF-I (ARF+IGF-I) or plus des-IGF-I (ARF+des-IGF-I) or renal arterial occlusion plus excipient (ARF Control); laparotomy only plus IGF-I (LAP+IGF-I) or laparotomy only plus excipient (LAP Control); also included was a group of rabbits given no treatment (Normal). Only those rabbits surviving to day 2 were entered into the study, phlebotomized, and weighed daily. In addition, animals surviving to day 7 were sacrificed, organ wet weights obtained, and kidneys taken for cortical tissue ion uptake measurements. Due to mortality and timing of cohort studies, the kidneys from five IGF-I-treated and three excipient-treated animals were not used for ion uptake studies. (See the following table for groupings, abbreviations, and sample size.)

| Treatment Groups | Serum Chemistry* (N = ) | Cortical Slice** (N = ) |
|---|---|---|
| I. Renal Arterial Occlusion + Excipient (ARF Control) | 11 | 6 |
| II. Renal Arterial Occlusion + des-IGF-I (ARF + des-IGF-I) | 10 | 3 |
| III. Renal Arterial Occlusion + IGF-I (ARF + IGF-I) | 13 | 10 |
| IV. Laparotomy + IGF-I (LAP + IGF-I) | 3 | 3 |
| V. Laparotomy + Excipient (LAP Control) | 2 | 2 |
| VI. Normal Untreated Control (Normal) | 2 | 4 |

*Includes rabbits who did not die on or before Day 2.
**Includes rabbits who lived to Day 7 when cortical slice experiment was run.

Preparation of the Animal Model

Weights were recorded pre-operatively and subsequently daily. Blood (1 cc) was drawn from an ear artery. In cohorts of six, rabbits were anesthesized with 1.7 ml of Hypnorm ™ i.m., administered 20 minutes before surgery, and given further doses three times intraoperatively for a total of 2.3 ml Hypnorm TM, or 0.4 ml/kg/hr.

Once anaesthetized, the animals were shaved, cleansed, and draped, and the peritoneal cavity was exposed through a midline incision. Using blunt dissection, right then left renal arteries were freed and clamped with Serrefin TM brand clips (Baby Dieffenbach Serrefin; Harvard Apparatus; Cat. #52-3241 or 52-3258). Concurrent with arterial occlusion, either one Alzet TM osmotic pump (Alza Corporation, Palo Alto, Calif., Model 2ML-1) containing 2.0 ml of 3.3 mg des-IGF-I/ml acetic acid (100 mM, pH 4.5), or 2 Alzet TM osmotic pumps each containing 2.0 ml of either recombinant-human IGF-I as described above (5.0 mg/ml in sodium chloride/sodium acetate buffer, pH 6.0) or its excipient were placed in the abdominal cavity. These pumps were primed to operate immediately upon placement. Each pump delivered 10.58 $\mu$l/hr, giving treated animals a total of approximately 0.364 mg/kg/day of des-IGF-I or 1.1 mg/kg/day of IGF-I per animal. Thus, the administered dose of des-IGF-I was one-third the dose of IGF-I. The control animals received excipient-filled pumps. Animals were then covered with saline-soaked gauze and placed aside for two hours until reperfusion.

After two hours of arterial occlusion the clips were removed and reperfusion was visually verified. The abdominal wall was closed with 0.0 Prolene TM, overlying skin sutured with 2.0 Prolene TM, and knots were buried under the skin to prevent irritation. The animals were then transferred to 35° C. heating pads, placed in prone position, and incubated until conscious (approximately 4-5 hours), after which they were removed to maintenance cages and provided with food and water for the remainder of the experimental period.

Data Collection

On post-occlusion days 1-6, 1.0 cc blood was collected from an ear vein, centrifuged for 10 minutes, and the serum was stored at $-80°$ C. When each group of six rabbits was completed, samples were thawed at room temperature and analyzed on a Monarch 2000 Chemical Systems Instrument (Allied Instrument Laboratories, Lexington, Mass.) for creatinine, urea nitrogen, glucose, sodium, potassium, calcium, cholesterol, albumin, alkaline phosphatase (ALP), and gamma-glutamyl transferase (GGT). On day 7, rabbits were euthanized and the right kidney, liver, spleen, heart, and thymus were harvested and weighed. Organs were fixed in formalin and sent for histological evaluation. In addition, the left kidney was harvested and weighed, and cortical slices were used for in vitro ion uptake studies, as described below.

The complete and consistent occlusion of the renal arteries in the study animals was confirmed by elevated serum urea nitrogen and serum creatinine levels. In animals exposed to the laparotomy only, the serum creatinine levels remained relatively constant and below 1.6 mg/dL in all cases, and the serum urea nitrogen levels remained below 10 mg/dL in all cases. In animals to which the supposed occlusion was administered, the creatinine levels in all cases rose above 3.5 mg/dL and the urea nitrogen levels rose above 65 mg/dL (N=48).

Renal Cortical Tissue Preparation

Immediately following sacrifice the left kidneys were decapsulated and cut along the horizontal axis in 1-cm thicknesses and placed in chilled phosphate buffered saline (PBS). Renal cortex was then sliced from the perimeter of each horizontal section and placed in a Stadie-Riggs TM tissue slicer, where eighteen 0.3-0.4-mm slices of approximately 30-100 mg were cut from each kidney, the outermost slices being discarded. Slices were then individually incubated at 25° C. in a medium of $^{14}$C-TEA and $^{3}$H-PAH with a 100% $O_2$ atmosphere, and constantly agitated at 70 cycles/min. for periods of 0, 15, 30, 45, 60, and 90 minutes, with three slices removed at each time period. Incubation medium consisted of 20 ml Cross and Taggart PAH buffer (72.8 $\mu$g/l PAH, 10.78 g/l $Na_2HPO_4.7H_2O$, 1.33 g/l $KH_2PO_4$, 1.48 g/l $MgSO_4.7H_2O$, 35.07 g/l NaCl, 1.49 g/l KCl), as described by Cross and Taggard, *Amer. J. Physiol.*, 161: 181-190 (1950), 10 ml lactate (0.90 g/100 ml), and 55 ml deionized water, with the pH adjusted to 7.4 using 1M NaOH. Two ml of $CaCl_2.2H_2O$ (0.736 g/100 ml) was then added, and the final volume was adjusted to 100 ml with deionized water. Prior to addition of kidney tissue, the medium was aerated with 100% oxygen for 30 minutes. Immediately before use, $^{14}$C-PAH and $^{3}$H-TEA were added in concentrations of 0.334 $\mu$Ci/3 ml medium.

At the specified times, slices were removed from the incubation medium, blotted dry, weighed, dissolved in 1.0 ml Protoso TM (New England Nuclear, Boston, Mass.), and neutralized with hydrochloric acid. Radioactivity in each kidney slice and 1.0 ml of its medium was measured using a LS5000TD Liquid Scintillation System (Beckman Instruments, Fullerton, Calif.). Results are reported as dpm (disintegrations per minute) per 100 mg of incubated tissue divided by dpm of 100 $\mu$L incubation medium. Mean and SEM for each group of three slices per time period were calculated for each rabbit. From these values, mean slice/medium ratios and SEMs were calculated for ARF+IGF-I, ARF+des-IGF-I, ARF Control, Normal, and LAP+IGF-I groups.

Statistical Analysis

Data were analyzed between groups on each day with Students T-test, and six- or three-day trends were evaluated for significance using a 2-factor repeated measure ANOVA using treatment and days as the two classifications. Histological qualities of tissue samples were classified on a scale ranging from normal to severe change in each of several categories, with statistical differences calculated using Fischer's test.

Data from the groups of rabbits were analyzed individually, and if no weight-related difference was discovered, data were pooled. Effective renal ischemia was verified visually at the time of surgery, as well as by post-operative elevations in creatinine. In non-occluded rabbits, post-operative creatinine remained below 1.6 mg/dL on all days. Rabbits receiving renal arterial clamping, on the other hand, demonstrated Day creatinine of 2.00-7.10 mg/dL, with day 7 renal histology verifying signs of ARF. Because renal arterial clamping resulted in measurable changes consistent with ARF in all rabbits, the validity of the experimental model was accepted.

Results: des-IGF-I v. Control

Rabbit Body Weight

Figure 3:
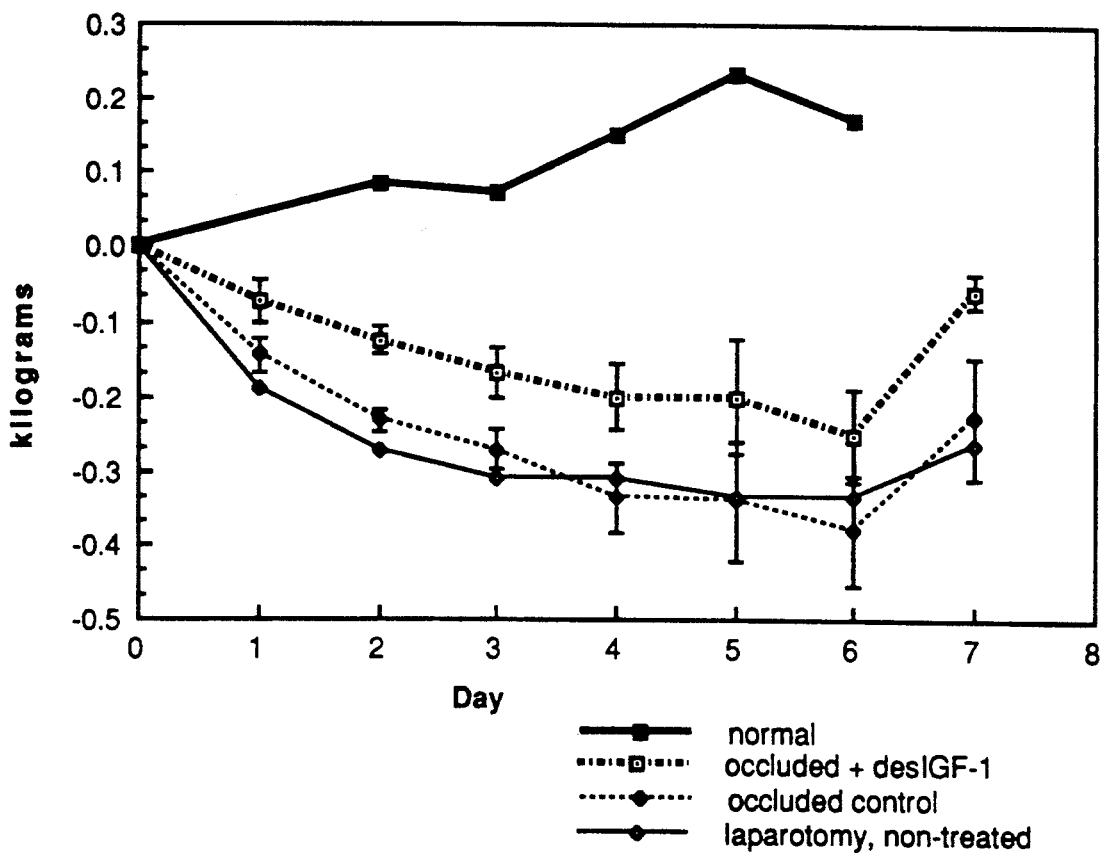
FIG. 3 is a graph of daily weight in des-IGF-I-treated and control-occluded rabbits over a seven-day period, with dotted solid squares being normal, dotted open squares being occluded plus des IGF-I, solid diamonds being occluded control, and open diamonds being laparotomy, non-treated. Des-IGF-I is an analogue of IGF-I.

Post-operatively, the untreated rabbit experienced an average weight loss of nearly 15% over 7 days (see Table 7 and FIG. 3). This translates to more than 350 mg by Day 6 in the occluded, non-treated animal. When des-IGF-I was given, the animal still experienced weight loss, but the loss was significantly less than with the untreated group, with an average loss of only 200 mg, a nearly 40% better performance.

An ANOVA reveals non-significant p values for all days except for Day 2 where p=0.0055. However, a 2-factor ANOVA using Day and Weight versus Group revealed an overall p value of 0.048.

The groups exposed to the laparotomy without the occlusion also experienced significant weight loss after the operation, losing nearly the same total body weight by Day 6 as did the occluded, non-treated rabbits. The non-treated laparotomy group of N=2 had lost an average of 335 mg by Day 6. The IGF-I-treated laparotomy group lost 243 mg by Day 6. There was no significant difference between the IGF-I-treated laparotomy group and the non-treated laparotomy group, nor was there a significant difference between the IGF-I-treated laparotomy group and the occluded, non-treated group. The importance of this finding will be discussed below.

TABLE 7

Daily Weight Loss (kg): des-IGF-I treated v. control

| Day X-Day 0 | des | SEM | Control | SEM | N = (cl. + des) | lap | SEM |
|---|---|---|---|---|---|---|---|
| Day 1-0 | −.07 | .028 | −.15 | .022 | (4,4) | −.19 | .03 |
| Day 2-0 | −.13 | .02 | −.23 | .015 | (4,4) | −.27 | .05 |
| Day 3-0 | −.17 | .033 | −.27 | .028 | (4,4) | −.31 | .06 |
| Day 4-0 | −.20 | .042 | −.34 | .047 | (4,4) | −.31 | .1 |
| Day 5-0 | −.20 | .077 | −.34 | .08 | (4,4) | −.34 | .15 |
| Day 6-0 | −.25 | .061 | −.38 | .076 | (9,8)* | −.34 | .21 |
| Day 7-0 | −.06 | .023 | −.23 | .08 | (3,4)** | −.27 | .24 |

*Day 6 values include 9 additional rabbits from same protocol whose daily weight was not measured, but whose on Day 6 was known.
**One control (cl.) rabbit died on Day 6.

Organ Weights

Figure 4:
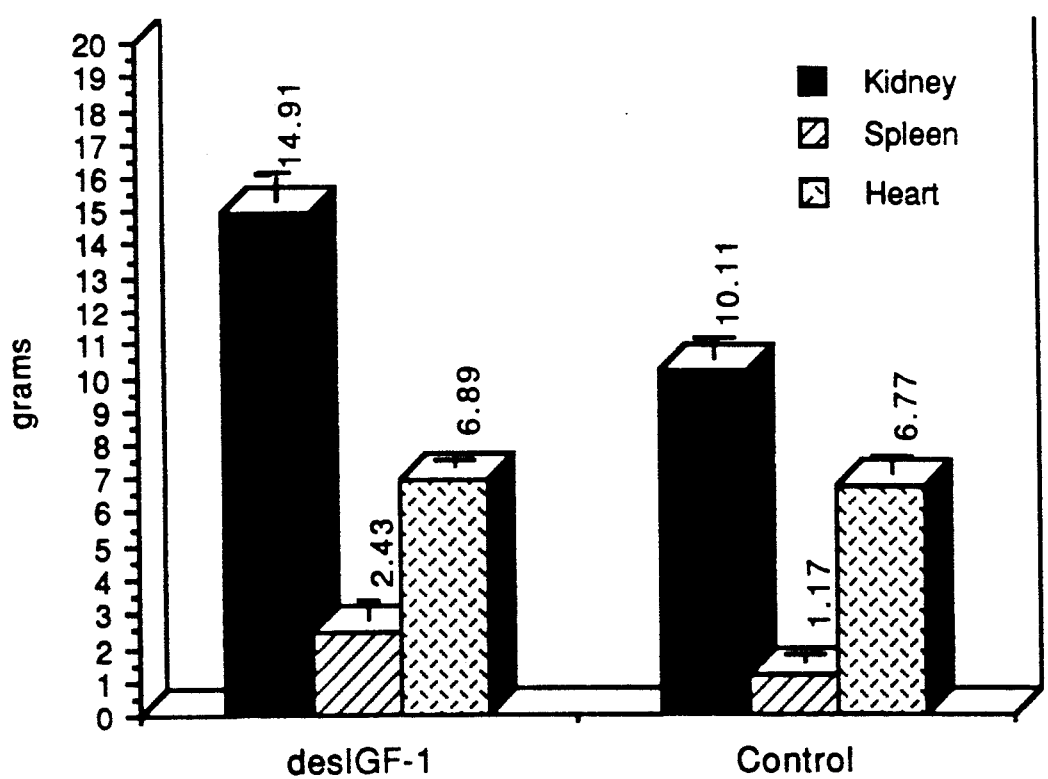
FIG. 4 is a graph of organ weights in des-IGF-I-treated and control-occluded rabbits for kidney (solid), spleen (one diagonal), and heart (two types of diagonals). The analysis of variance (ANOVA) p value was significant for kidney (0.0004) (control [cl.] N=7, des N=9), and for spleen (0.028) (cl. N=7, des N=8), but not statistically significant for heart (0.84) (cl. N=6, des N=4).

In the des-IGF-I-treated animals, analysis of the kidney weight (right kidney only) revealed that the mean kidney weight of the des-IGF-I-treated animals (N=9) was 1.5 times greater than that of the occluded, non-treated controls (N=7) (14.87±0.774 g versus 10.21±0.61 g, respectively, p=0.0004). Spleen weight in the treated animals was twice that of the control group(2.43±0.44 g versus 1.17–0.21 g, respectively, p=0.028). There was no difference between groups for heart weight, and thymus weight was not measured in this first group of the study. See FIG. 4.

Serum Creatinine Levels

Figure 5:
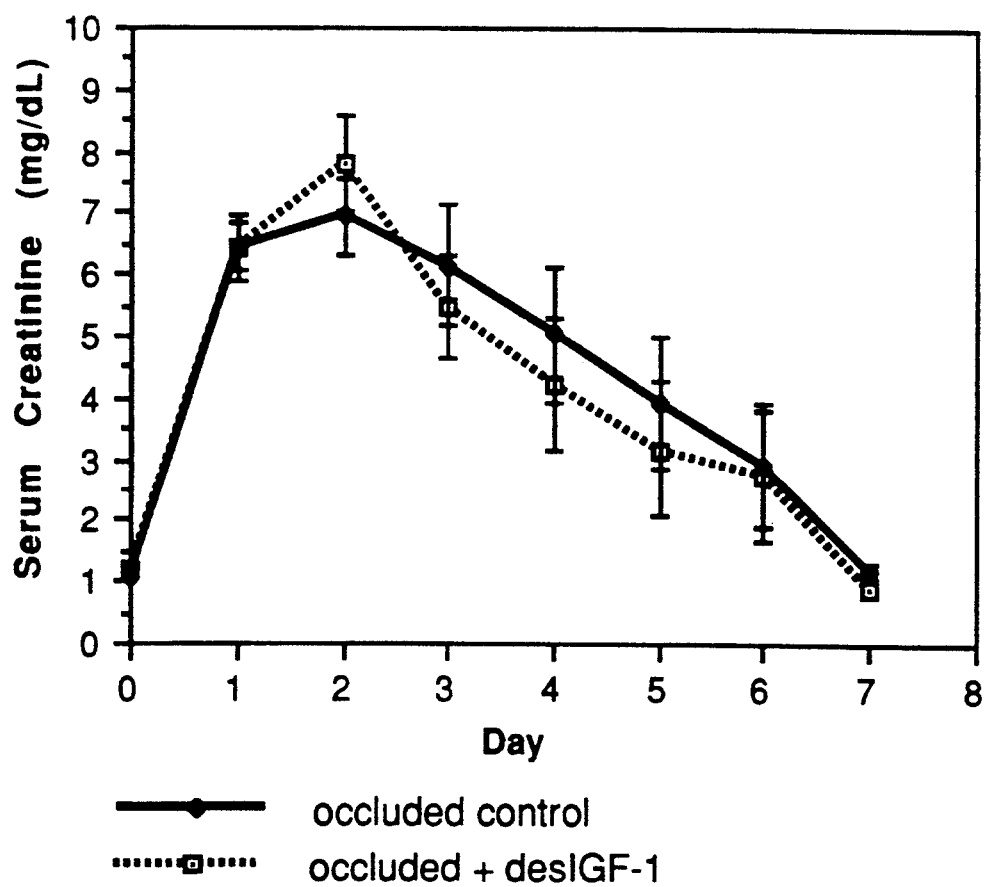
FIG. 5 is a graph of serum creatinine levels over 7 days in des-IGF-I-treated, occluded (squares) and control-occluded (diamonds) rabbits.

In all rabbits, post-occlusion serum creatinine levels elevated from a control average of 1.14±0.8 mg/dL to a post occlusion high on Day 2 of 7.8±0.77 and 6.9±0.63 mg/dL for des-IGF-I-treated and control groups, respectively (p=0.7). In both groups these elevated levels returned to normal levels of 0.9±0.15 and 1.18±0.12 mg/dL, respectively, by Day 7, and at no point were the levels of serum creatinine statistically different between the two groups (Table 8 and FIG. 5).

Serum Urea Nitrogen Levels

Figure 6:
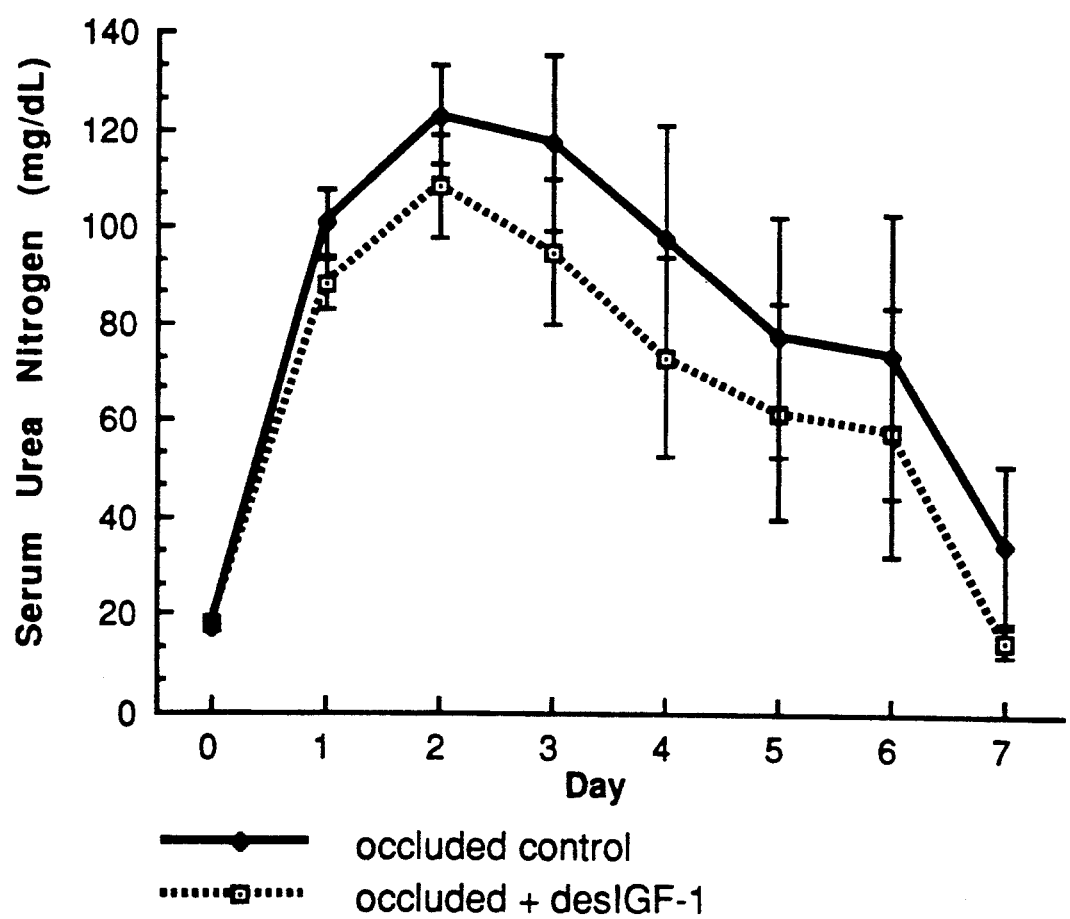
FIG. 6 is a graph of serum urea nitrogen levels over 7 days in des-IGF-I-treated, occluded (squares) and control-occluded (diamonds) rabbits.

Post-occlusion serum urea nitrogen levels elevated from normal levels of 17.7±0.7 mg/dL to a high on Day 2 of 125±9.3 mg/dL in the control group and 110±9.3 mg/dL in the treated group. In the control group, these levels then regressed to a low on Day 6 of 74±29.6 mg/dL, while the des-IGF-I-treated animals returned to 58±25.6 mg/dL. Though the ANOVA between the groups on any given day was not statistically significant, the 2-factor repeated measure of Urea Nitrogen level and Day versus Group resulted in p=0.058, and the mean levels on any given day for the treated group were always lower than the levels in the untreated group. See Table 8 and FIG. 6.

Serum Glucose Levels

Serum glucose levels in both the occluded des-IGF-I-treated and the occluded control animals decreased post-operatively from an average starting level of 173±22 mg/dL to Day 1 values of 101±8.5 mg/dL and 125±15.4 mg/dL, respectively. After Day 1, levels elevated to approximately 140 mg/dL in both groups, and remained between 127 and 165 mg/dL throughout the rest of the experiment. The IGF-I-treated animals experienced the same decline in serum glucose post-operatively. The starting mean of 164 mg/dL declined to a Day 1 low of 103±4.0 mg/dL in the IGF-I group, and 129±7.0 mg/dL in the control group. Subsequent levels remained within the range of 122 to 170 mg/dL. See Table 8.

TABLE 8

Serum Levels of Creatinine, Urea Nitrogen, and Glucose in des-IGF-I-Treated versus Control-Occluded Rabbits

| | Day: | | | | | | | |
|---|---|---|---|---|---|---|---|---|
| | 0 | 1 | 2 | 3 | 4 | 5 | 6 | 7 |
| Creatinine | | | | | | | | |
| des-IGF-I mean | 1.18 | 6.45 | 7.80 | 5.45 | 4.24 | 3.16 | 2.72 | 0.90 |
| des-IGF-I SEM | ±.10 | ±.39 | ±.77 | ±.83 | ±1.07 | ±1.10 | ±1.06 | ±.15 |
| control mean | 1.09 | 6.44 | 6.94 | 6.16 | 5.03 | 3.92 | 2.93 | 1.18 |
| control SEM | ±.05 | ±.52 | ±.63 | ±.97 | ±1.11 | ±1.07 | ±1.00 | ±.12 |
| N = (cl, des) | 9,10 | 9,10 | 9,10 | 9,10 | 9,10 | 9,9* | 8,9** | 4,3 |
| 2-factor ANOVA for treatment and Day1-Day7 versus Group gives p = 0.29. | | | | | | | | |
| Urea Nitrogen | | | | | | | | |
| des-IGF-I mean | 18 | 91 | 110 | 98 | 82 | 62 | 58 | 15 |
| des-IGF-I SEM | ±.9 | ±5.7 | ±9.3 | ±14.0 | ±20.7 | ±22.1 | ±25.6 | ±3.2 |
| control mean | 17 | 102 | 125 | 126 | 111 | 93 | 74 | 19 |
| control SEM | ±0.8 | ±6.0 | ±9.3 | ±18.6 | ±24.4 | ±27.2 | ±29.6 | ±1.8 |
| N = (cl, des) | 9,10 | 9,10 | 9,10 | 9,10 | 9,10 | 9,9 | 8,9 | 5,4 |
| 2-factor ANOVA for treatment and Day1-Day7 versus Group gives p = 0.058. | | | | | | | | |
| Glucose | | | | | | | | |
| des-IGF-I mean | 177 | 101 | 143 | 137 | 131 | 131 | 139 | 127 |
| des-IGF-I SEM | ±20.1 | ±8.5 | ±8.0 | ±4.2 | ±6.4 | ±7.5 | ±15.8 | ±3.7 |

TABLE 8-continued

Serum Levels of Creatinine, Urea Nitrogen, and Glucose in des-IGF-I-Treated versus Control-Occluded Rabbits

| | Day: | | | | | | | |
|---|---|---|---|---|---|---|---|---|
| | 0 | 1 | 2 | 3 | 4 | 5 | 6 | 7 |
| control mean | 168 | 125 | 148 | 148 | 165 | 160 | 154 | 133 |
| control SEM | ±9.5 | ±15.4 | ±8.0 | ±3.8 | ±18.6 | ±20.0 | ±16.5 | ±5.5 |
| N = (cl, des) | 9,10 | 9,10 | 9,10 | 9,10 | 9,10 | 9,9 | 8,9 | 5,4 |

2-factor ANOVA for treatment and Day1-Day7 versus Group gives p = 0.09

*Treated rabbit #4 died.
**Control rabbit #7 died.

Results: IGF-I v. Control

Rabbit Body Weight

Data from the control rabbits used in the IGF-I experiments were not combined with the data from the control rabbits used in the des-IGF-I experiments, even though the protocol for both control groups was the same. As expected, ARF led to significant weight loss post-operatively in all rabbits. ARF controls showed an average deficit of 376±84 g on Day 6, a 15% loss of initial body weight. Unlike des-IGF-I, however, IGF-I-treated rabbits lost 250±50 g by Day 6, a 9.5% loss, p=0.34. An ANOVA reveals non-significant p values for all days and a 2-factor ANOVA using Day and Treatment versus Group of 0.62. See Table 9. There is also no significant difference between ARF+IGF-I and LAP+IGF-I groups.

TABLE 9

| Daily Weight Loss (kg): IGF-I-Treated v. Control | | | | | |
|---|---|---|---|---|---|
| DayX-Day0 | IGF-I | SEM | control | SEM | N = (cl., IGF-I) |
| Day 1-0 | -.10 | 0.01 | -.11 | .02 | (11,13)* |
| Day 2-0 | -.25 | 0.03 | -.26 | .02 | (11,13) |
| Day 3-0 | -.29 | 0.03 | -.30 | .03 | (6,10)** |
| Day 4-0 | -.30 | 0.03 | -.35 | .04 | (9,12) |
| Day 5-0 | -.32 | 0.04 | -.36 | .05 | (9,12) |
| Day 6-0 | -.25 | 0.05 | -.38 | .08 | (9,12) |
| Day 7-0 | -.21 | 0.07 | -.30 | .14 | (4,6)*** |

*Includes rabbits 25-42 and 44-49.
** Controls #40, 42, and 44, and IGF-I-treated died on Day 3. In addition, rabbits 45-49 were not weighed on Day 3.
***Includes only weights of rabbits 31-42. Previous rabbits were sacrificed on Day 6.

Organ Weights

In the IGF-I-treated animals, Day 7 kidney weight equalled that of the control group kidneys. Average IGF-I-treated kidney weight was 11.85±0.62 g, while non-treated kidney weight was 10.19±0.65 g, and an ANOVA gave a p value of 0.10.

The average wet weight of the thymus in the IGF-I-treated group was nearly twice as large as the control thymus, 4.7±0.4 g and 2.7±0.6 g, respectively, with a significant ANOVA p value of 0.02. When thymus size is corrected to the rabbit body weight, the probability that the thymus mean weights are representative of significant treatment related differences increases (p=0.01). However, a comparison between normal rabbit thymus weight and ARF+IGF-I thymus weight showed that the treated and normal rabbits had similar mass thymuses.

Figure 7:
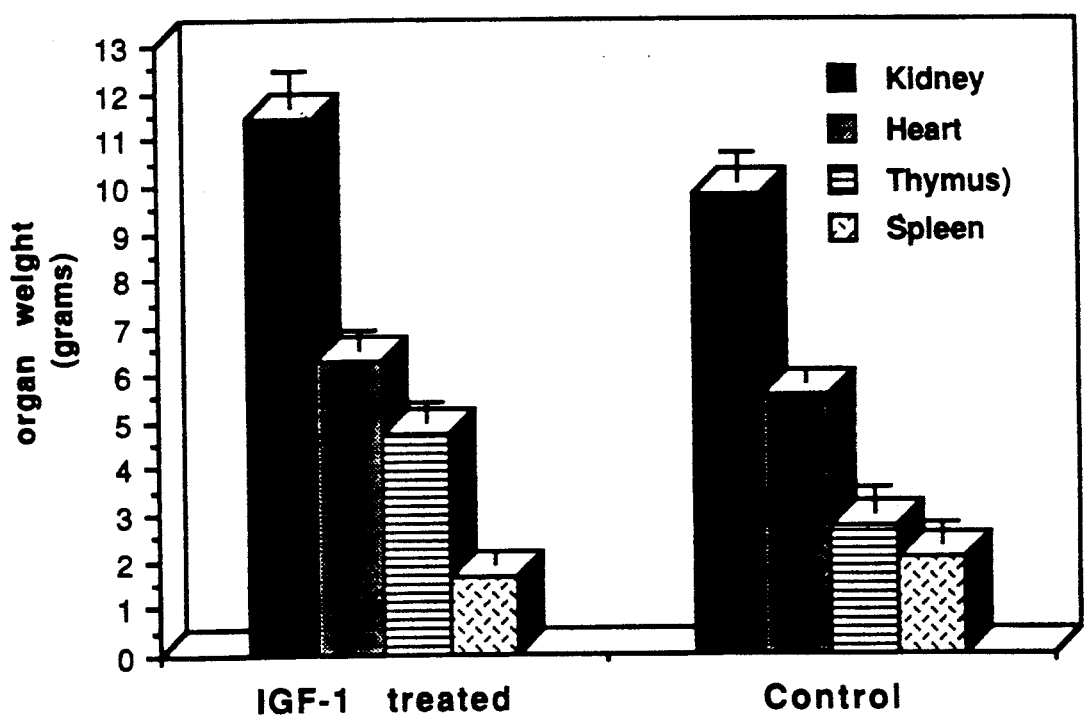
FIG. 7 is a graph of organ weights of IGF-I treated and control rabbits, where the solid bars represent kidney, the dotted bars represent heart, the horizontal line bars represent thymus, and the opposite diagonal bars represent spleen.

The spleens in the two groups were of similar size, 1.7±0.3 g and 2.0±0.5 g for IGF-I-treated and control groups, respectively. As with des-IGF-I, the heart was of similar size, regardless of treatment, and the livers in the IGF-I-treated animals showed no differences in size. See Table 10 and FIG. 7. Six animals were not weighed and four others died before day 7; therefore, these data include ten treated and six control rabbits.

TABLE 10

Organ Weights in IGF-I-Treated and des-IGF-I-Treated and Control-Occluded Rabbits

| Group | Kidney | Spleen | Thymus | Heart | Liver | N = (K,S,T,H,L)* |
|---|---|---|---|---|---|---|
| IGF-I | 11.9 | 1.7 | 4.7 | 6.3 | 61.6 | (10,10,6,10,10)** |
| SEM | ±0.06 | ±0.3 | ±0.4 | ±0.3 | ±2.9 | |
| ARF Cl. | 10.2 | 2.0 | 2.7 | 6.3 | 72.3 | (6,6,4,6,6)** |
| SEM | ±0.7 | ±0.5 | ±0.6 | ±0.3 | ±6.5 | |
| des | 14.9 | 2.4 | — | 6.9 | — | (9,8,0,4,0)*** |
| SEM | ±0.8 | ±0.4 | ±0.2 | — | | |
| des Cl. | 10.1 | 1.2 | — | 6.8 | — | (7,7,0,6,0) |
| SEM | ±0.6 | ±0.2 | — | ±0.5 | — | |
| Normal | 7.0 | 1.4 | 5.2 | 5.8 | 87.0 | N = 2 |
| SEM | ±0.4 | ±0.3 | ±1.7 | ±0.7 | ±25.2 | |

*K = Kidney, S = Spleen, T = Thymus, H = Heart, L = Liver.
**In rabbits 31-42, IGF-I-treated animals (N = 6) and control animals (N = 4) had all organs weighed. In rabbits 25-30, IGF-I-treated animals (N = 4) and control animals (N = 2) had all organs weighed except thymus.
***In des-IGF-I-treated rabbits 1-23, all 9 des-IGF-I-treated animals and all 7 control animals surviving to Day 7 had kidneys weighed. Treated rabbit #13 did not have spleen weight recorded, and 5 treated as well as one control rabbit did not have hearts weighed, though no difference in size or histology was noted. Thymus and liver weights were not recorded in this group of animals, but no size difference between groups was visibly noted.

Serum Creatinine Levels

Figure 8:
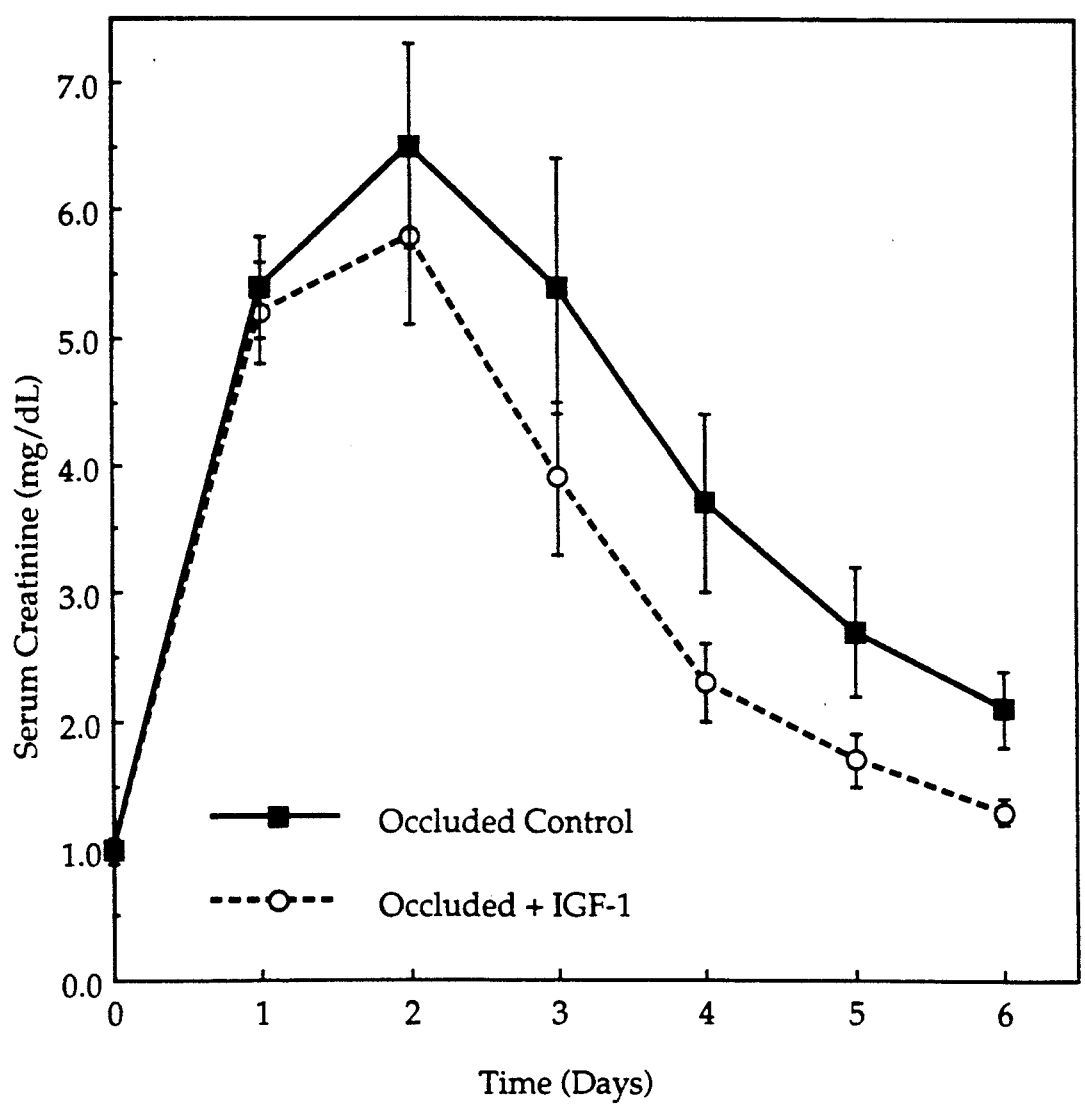
FIG. 8 is a graph of the serum creatinine levels over 6 days in IGF-I-treated, occluded (squares) and control-occluded (diamonds) rabbits.

Animals in the IGF-I-treated and non-treated groups also experienced a post-operative elevation in serum creatinine levels from normal value on Day 1 of 1.00±0.09 to highs on Day 2 of 5.8±0.7 mg/dL and 6.5±0.8 mg/dL, respectively. In both groups these elevated levels returned on Day 7 to near normal levels of 1.17±0.12 and 1.2±0.06 in treated and control groups, respectively. On Days 5 and 6, the IGF-I-treated animals had significantly lower serum creatinine levels than the control groups, p=0.04 and 0.01, respectively. On these days, the treated animals had creatinine values that were 40% less than the control groups. Though the overall 2-factor ANOVA was not significant (p=0.192 for Days 1 to 6), effects of the drug are possibly seen in the latter stages of the recovery, Days 4 to 6. 2-Factor ANOVA for these days was significant (p=0.0334). See Table 11 and FIG. 8.

Serum Urea Nitrogen Levels

Figure 9:
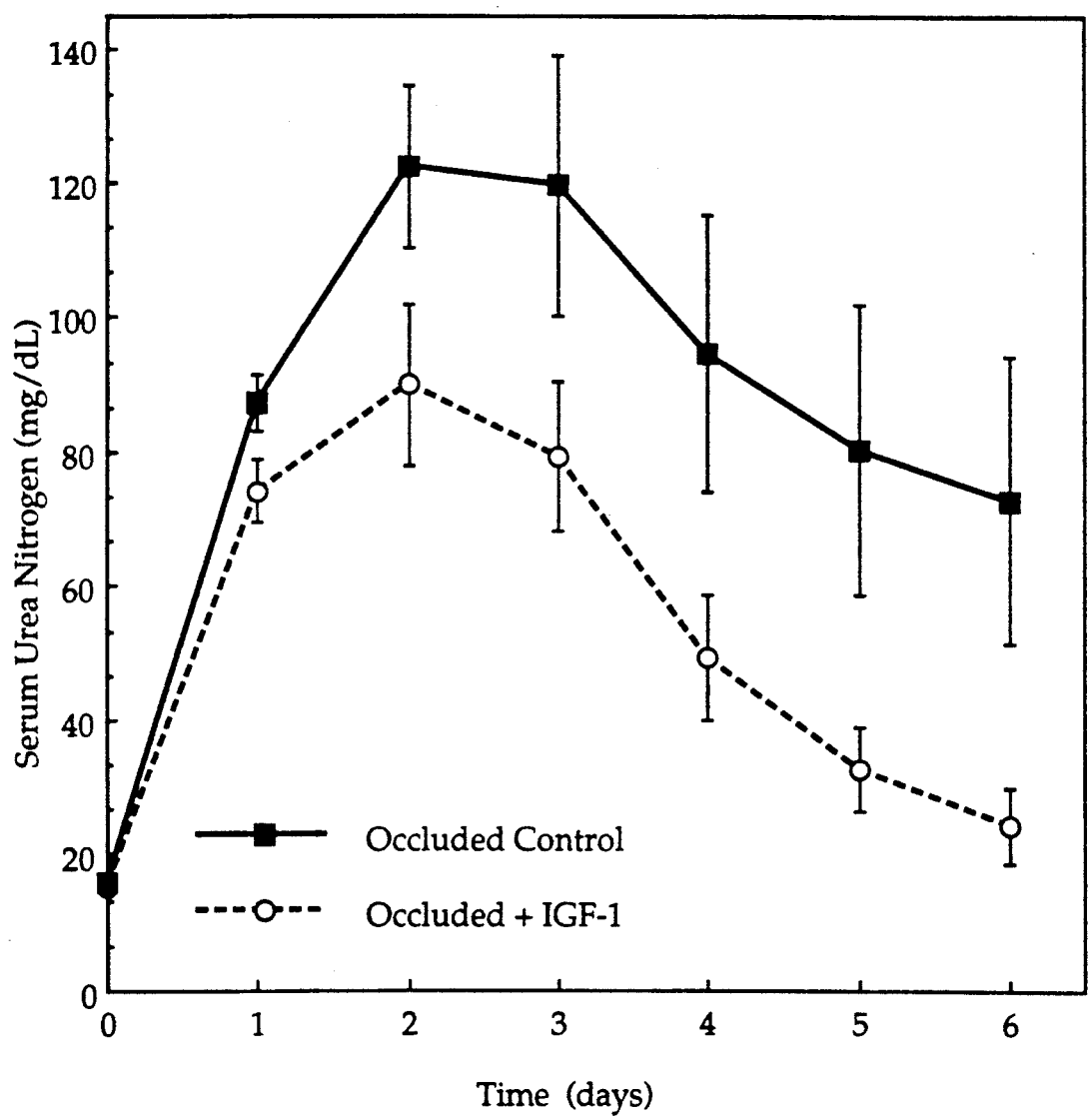
FIG. 9 is a graph of serum urea nitrogen levels over 6 days in IGF-I-treated, occluded (squares) and control-occluded (diamonds) rabbits.

Animals in the IGF-I-treated and non-treated groups had elevated post-occlusion serum urea and nitrogen levels. A baseline average of 15.5±0.7 mg/dL on Day 0 rose to 122.4±12.1 mg/dL on Day 2 in the ARF controls and 89.9±12.0 mg/dL in ARF+IGF-I animals. By Day 7, both groups had returned to near normal levels at below 20±5.5 mg/dL each. An ANOVA shows that daily differences were statistically significant on Days 1, 4, 5, and 6, and 2-factor ANOVA of treatment against both Day and serum urea nitrogen level from Day 1 to Day 6 reveals a p value of 0.0348. See Table 11 and FIG. 9.

ratio of 4.61±0.82 in the occluded control animals (p=0.16). The ratios at 45 and 60 minutes were significantly decreased (p=0.052 and 0.043, respectively), and the 2-factor ANOVA was near significant at p=0.077. The 90-minute ratio in occluded, IGF-I-treated animals rose to a value of 5.09±0.56, but was not significantly different from the 90-minute ratio of the occluded control group (p=0.64).

Figure 10:
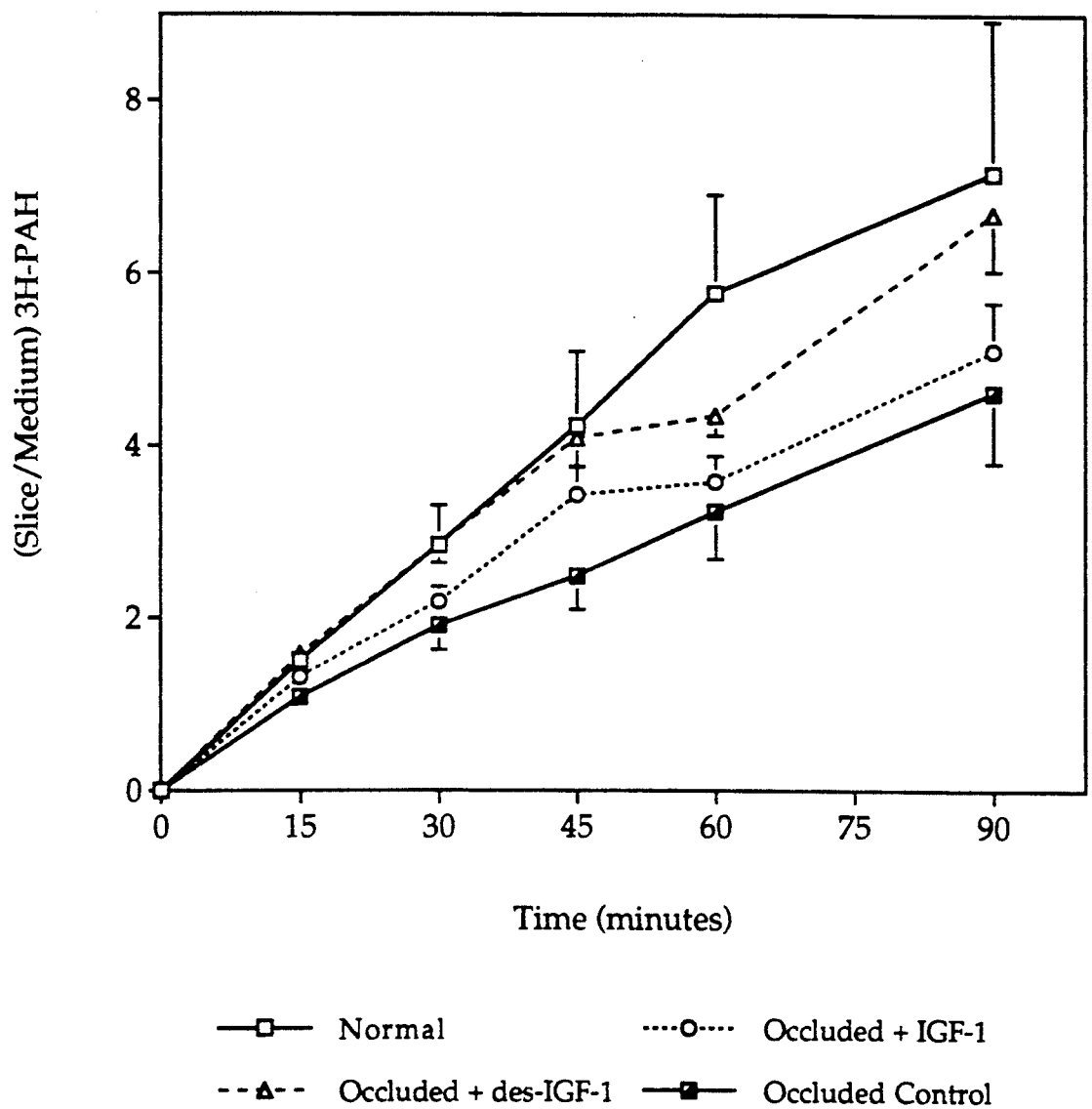
FIG. 10 is a graph of 3H-p-aminohippurate $^3$H-PAH) uptake over 90 minutes by renal cortical tissue. The open diamond bars represent normal, the open square bars with dots represent occluded+des-IGF-I, the solid square bars with dots represent occluded+IGF-I, and the diamond bars represent occluded control.

The des-IGF-I-treated groups also displayed improved concentrating ability over the controls, but significant difference was not observed at any time points. See Table 12 and FIG. 10.

$^{14}$C-TEA

Uptake of the organic cation TEA reached a value of 7.36±1.40 at 90 minutes in normal rabbit renal cortical slices. In the occluded control animals, this value dropped significantly to 4.83±0.50, which represents a 35% decrease in concentrating ability.

In the IGF-I-treated animals, the ratio at ninety minutes was 7.21±0.80, and the values at all time points were increased compared to the occluded control animals, with significance at all time points, and a 2-factor ANOVA comparing Time and Group against Ratio of p=0.0014.

TABLE 11

Serum Levels of Creatinine. Urea Nitrogen, and Glucose in IGF-I-Treated versus Control-Occluded Rabbits

| | Day: | | | | | | | |
|---|---|---|---|---|---|---|---|---|
| | 0 | 1 | 2 | 3 | 4 | 5 | 6 | 7 |
| Creatinine | | | | | | | | |
| IGF-I mean | 1.0 | 5.2 | 5.8 | 3.9 | 2.3 | 1.7* | 1.3* | 1.2 |
| IGF-I SEM | 0.03 | 0.4 | 0.7 | 0.6 | 0.3 | 0.2 | 0.1 | 0.1 |
| control mean | 1.0 | 5.4 | 6.5 | 5.4 | 3.7 | 2.7 | 2.1 | 1.2 |
| control SEM | 0.1 | 0.4 | 0.8 | 1.0 | 0.7 | 0.5 | 0.3 | 0.06 |
| 2-Factor ANOVA for Treatment and Day4–Day6 versus Group gives p = 0.03. | | | | | | | | |
| Urea Nitrogen | | | | | | | | |
| IGF-I mean | 15.3 | 74.2 | 89.9 | 79.2 | 49.4 | 32.8 | 24.4 | 19.0 |
| IGF-I SEM | 0.6 | 4.7 | 12.0 | 11.2 | 9.3 | 6.3 | 5.5 | 5.5 |
| control mean | 15.9 | 87.3 | 122.4 | 119.7 | 94.6 | 80.3 | 72.8 | 14.5 |
| control SEM | 0.7 | 4.1 | 12.1 | 19.5 | 20.6 | 21.6 | 21.3 | 0.5 |
| p value | 1.0 | 0.05 | 0.07 | 0.07 | 0.04 | 0.03 | 0.02 | — |
| N = (cl,IGF) | 11,13 | 11,13 | 11,13 | 10,13 | 9,12 | 9,12 | 9,12** | 2,6*** |
| 2-factor ANOVA for treatment and Day1–Day6 versus Group gives p = 0.0348. | | | | | | | | |

*p < 0.05. See text for exact values.
**Control rabbits 40 and 42 died on Days 3 and 4, respectively. Treated rabbit 45 died on Day 4. The last creatinine measures of the three rabbits before death were 10.00, 11.30, and 7.70 mg/dL, respectively, and the last urea nitrogen measures were 158, 215, and 147 mg/dL, respectively which, along with histological evaluation confirming excessive renal granulation and cellular necrosis, implicates renal failure as a cause of death.
***Day 7 serum values were not calculated in rabbits 25–30 and 43–48 (IGF-I-treated N = 3, control N = 3). In addition, control rabbit #36 died on Day 7 before being bled. Furthermore, lab data for control rabbit 32 showed a Day 7 serum urea nitrogen level of 14 mg/dL, while the Day 6 level was 150 mg/dL. This unlikely low value was discarded. The N for the creatinine levels on this day is N = 3 for the controls, since the Day 7 value was not unexpectedly abnormal.

$^3$H-PAH

Uptake of the organic anion PAH by cortical slices of renal tissue, as measured by the ratio of radiolabeled anion in the tissue to anion in the media, rose from a start of 0 at time zero to a level in normal rabbits of 7.15±1.78 at 90 minutes (N=4). After renal occlusion, anion uptake efficiency decreased to a 90-minute uptake In addition, there was no difference between the occluded, IGF-I-treated ratios and the normal ratios at any time point, and the 2-factor ANOVA using the same parameters gave a p value of 0.71.

Figure 11:
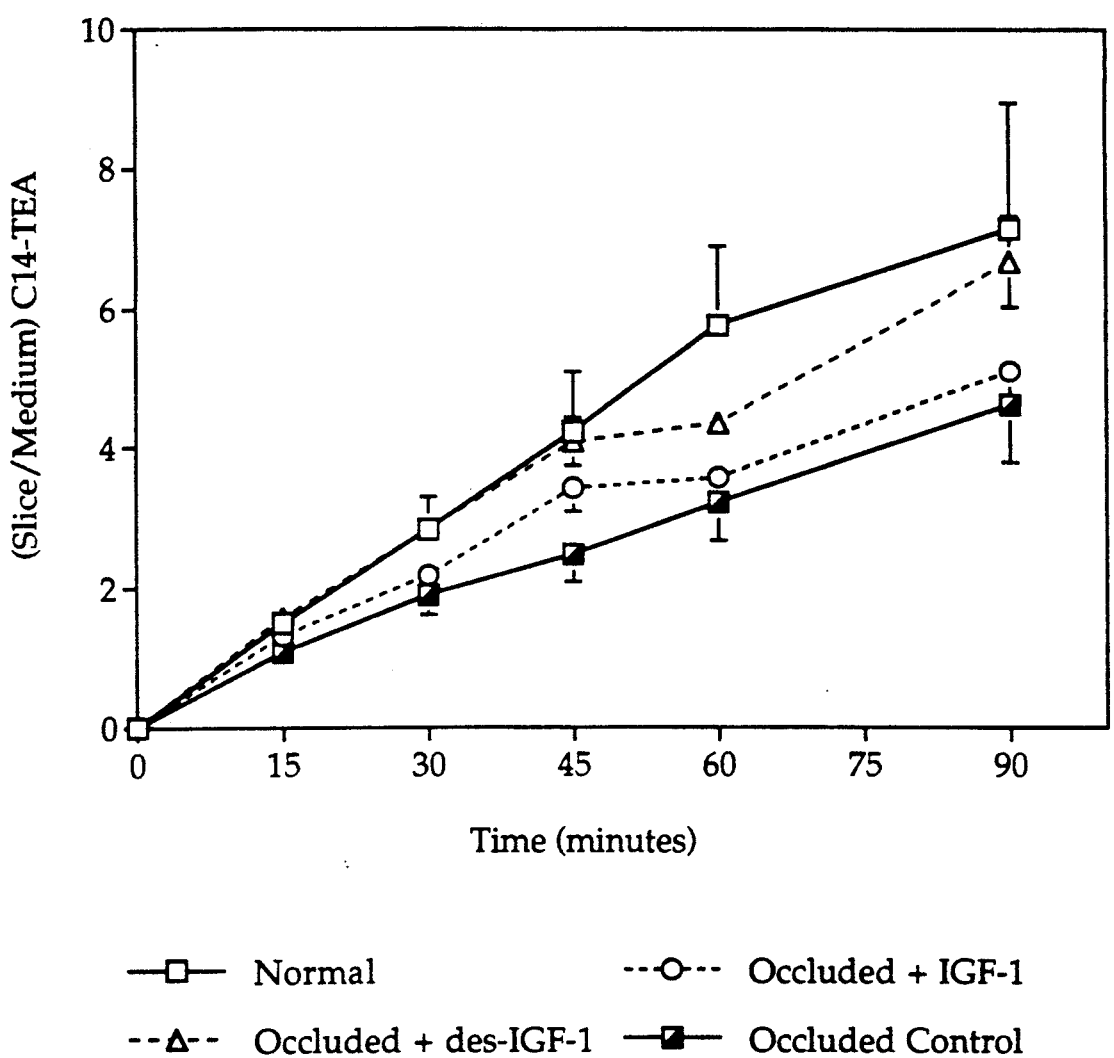
FIG. 11 is a graph of $^{14}$C-TEA uptake over 90 minutes by renal cortical tissue. The open square bars with dots represent occluded+des-IGF-I, the open square bars represent normal, the solid square bars with dots represent occluded+IGF-I, and the diamond bars represent occluded control.

The ninety-minute ratio of the des-IGF-I group was 8.48±1.04, which was also significantly increased over the occluded control animal's TEA uptake ratio. See Table 12 and FIG. 11.

TABLE 12

Organic Cation and Anion Uptake by Normal, Control Occluded, and des-IGF-I- and IGF-I-Treated Animals*

| Group | 0 min | 15 min | 30 min | 45 min | 60 min | 90 min | N = |
|---|---|---|---|---|---|---|---|
| $^3$H-PAH | | | | | | | |
| Normal | 0 | 1.50 | 2.84 | 4.22 | 5.76 | 7.15 | 4 |
| SEM | 0 | 0.08 | 0.46 | 0.86 | 1.14 | 1.78 | |

TABLE 12-continued

Organic Cation and Anion Uptake by Normal,
Control Occluded, and des-IGF-I- and IGF-I-Treated Animals*

| Group | 0 min | 15 min | 30 min | 45 min | 60 min | 90 min | N = |
|---|---|---|---|---|---|---|---|
| ARF Cl. | 0 | 1.08 | 1.90 | 2.48* | 3.22* | 4.61 | 10 |
| SEM | 0 | 0.14 | 0.28 | 0.39 | 0.54 | 0.82 | |
| des-IGF-I | 0 | 1.57 | 2.84 | 4.08** | 4.34 | 6.68 | 3 |
| SEM | 0 | 0.10 | 0.21 | 0.34 | 0.23 | 0.65 | |
| ARF + IGF-I | 0 | 1.31 | 2.18 | 3.42 | 3.57 | 5.09 | 10 |
| SEM | 0 | 0.12 | 0.18 | 0.33 | 0.30 | 0.56 | |
| LAP + IGF-I | 0 | 1.21 | 2.15 | 3.09 | 3.50 | 4.78 | 3 |
| SEM | 0 | 0.02 | 0.15 | 0.21 | 0.02 | 0.54 | |
| $^{14}$C-TEA | | | | | | | |
| Normal | 0 | 2.13 | 4.04 | 4.97 | 6.58 | 7.36 | 4 |
| SEM | 0 | 0.31 | 0.76 | 0.92 | 0.95 | 1.40 | |
| ARF Cl. | 0 | 1.31 | 2.23 | 2.86 | 3.60 | 4.83 | 10 |
| SEM | 0 | 0.10 | 0.19 | 0.26 | 0.37 | 0.50 | |
| ARF + des | 0 | 2.49 | 3.95 | 6.11 | 6.47 | 8.48 | 3 |
| SEM | 0 | 0.84 | 0.88 | 1.17 | 0.88 | 1.04 | |
| ARF + IGF-I | 0 | 2.01 | 3.25 | 4.85 | 5.18 | 7.21 | 10 |
| SEM | 0 | 0.15 | 0.25 | 0.54 | 0.32 | 0.80 | |
| p value*** | | 0.0012 | 0.0049 | 0.0036 | 0.0045 | 0.0192 | |
| LAP + IGF-I | 0 | 1.60 | 3.41 | 5.18 | 5.72 | 6.80 | 3 |
| SEM | 0 | 0.19 | 0.39 | 0.06 | 0.29 | 1.32 | |

Data expressed as ratio of ion in tissue slice to ion in media at the time interval indicated.
*Both these values are significantly lower than Normal.
**45-min. slice/medium ratio for des-IGF-I-treated is significantly greater than control.
***Significance between IGF-I-treated and control group. 2 factor ANOVA p = 0.0014. No difference between IGF-I and normal.

Histopathology

Animals surviving to the seventh day were sacrificed and organs obtained for histological evaluation (Table 13).

TABLE 13

Renal Histologic Scores* in ARF + IGF-I vs. ARF Control Rabbits

| Group | Degeneration | Congestion | Casts | Nephritis | Edema | Mineralization | Hypertrophy | Dilatation |
|---|---|---|---|---|---|---|---|---|
| ARF + IGF-I | 2.4 ±0.5 | 0.2 ±0.1 | 0.9 ±0.3 | 0.4 ±0.2 | 1.8 ±0.1 | 1.7 ±0.4 | 2.6 ±0.2 | 1.9 ±0.4 |
| ARF Cl. | 1.5 ±0.3 | 0.3 ±0.2 | 1.1 ±0.3 | 0.8 ±0.3 | 2.4 ±0.3 | 2.2 ±0.4 | 2.4 ±0.3 | 2.3 ±0.3 |

*Scale based on 0 to 4 rating, with 4 representing "severe" damage and 0 "normal."

No statistically significant differences were observed between groups for heart, spleen, or liver histology. Despite the large increase in thymic weight, evaluation of eleven control and six IGF-I-treated thymuses showed no significant morphological changes. Kidney sections for all animals with ARF showed tubular mineralization, dilatation, and degeneration.

Groups were evaluated for the presence of the following: chronic interstitial multifocal nephritis, edema, subacute capsular inflammation, medullary epithelial hypertrophy, and tubular mineralization, dilatation, degeneration, congestion, and hyaline casts. Sections were assigned values 0-4 based on absent, mild, moderate, marked, or severe changes. These values were averaged for each category and the means for each treatment group was compared using an unpaired two-tailed T-test. No significant differences were observed in any of these categories, but on average, IGF-I-treated rabbits tended to have less congestion, casts, nephritis, edema, mineralization, and dilatation, and treated rabbits tended to have more hypertrophy.

Discussion

These data suggest that IGF-I and des-IGF-I have clear beneficial effects on ischemic renal function in the rabbit. There was a favorable effect of des-IGF-I on weight loss that was improved by 40% in des-IGF-I-treated rabbits (p=0.048). The effect of IGF-I on weight loss was not as impressive nor was it statistically significant.

In many measures of anabolic effect des-IGF-I demonstrates at least a three-fold increased potency over sequence-complete IGF-I. However, even with the compensatory two-thirds reduction in dose used in the experiments herein, des-IGF-I-treated rabbits had renal weights 50% greater than the control rabbits over a seven-day period (p=0.0004). IGF-I-treated kidneys did not demonstrate the same renal mass increase, but both IGF-I and des-IGF-I enhanced renal recovery. This is an important point, as it appears that a beneficial effect of IGF-I on renal regeneration can be seen without a gross change in organ size.

There is widespread evidence in both groups of necrosis, granulation, and general cell damage. Some kidneys show areas of calcification, resultant from cell death, and there are also extracellular signs of protein deposition, causative of edema in both groups. There was evidence from histological examination that IGF-I-treated animals showed less renal damage and more evidence of renal regeneration.

Not only do the data show an increase in splenic, thymic, and renal mass, but the serum measures of creatinine and urea nitrogen suggest a specific improvement in renal function in both the des IGF-I- and IGF-I-treated groups. The IGF-I treated group demonstrated significantly lower levels of both serum creatinine and urea nitrogen when compared to the control rabbits. In the IGF-I-treated rabbits, the urea nitrogen levels were on average 50% less than the control values from Day 2 to Day 6. Excessive urea nitrogen is not desirable, and returning to normal levels as soon as possible can be regarded as a positive response. IGF-I-treated animals also displayed a more rapid return to normal levels of serum creatinine than did the controls, and this too suggests that the treatment with IGF-I improved the filtration and subsequent handling of ultrafiltrate by the kidney. In the des IGF-I-treated rabbits, serum creatinine levels were not lower than in the control group. Serum urea nitrogen levels, however, were marginally significantly lower (p=0.058). Thus, these data suggest that IGF-I is more effective than the truncated protein at increasing functional renal mass needed to decrease serum levels. It appears that IGF-I convincingly restores normal renal function in ARF more quickly and more dramatically than excipient with possible early changes at 24 hours.

The pro-renal effects of IGF-I are also found in the organic anion and cation studies. As mentioned above, renal handling of cations and anions by the basal and apial membranes is of clinical importance. In the studies herein, the ischemic insult clearly decreased the ability of the renal cortical slices to concentrate both anion and cation against the gradient in the experimental setup, a point which is verified by the significant difference between slice-to-medium ratios in normal rabbits and control occluded rabbits. The reductions in functional ability per unit mass were decreased by 35% for both ions.

When given the IGF-I, the animals did not exhibit a significant improvement in the ability of their renal tissue to concentrate the anion (though the trend suggests that with more subjects the errors might decrease and significance might be achieved). However, the IGF-I-treated animals did display a dramatically higher slice-to-medium ratio for the cation, both treated groups demonstrating normal concentrating ability. Thus, administration of IGF-I for seven days following the acute insult produced dramatic restoration of concentrating ability: TEA uptake increased by 70% and PAH uptake increased by 50% when compared to ARF controls. In other words, when given either IGF-I or des-IGF-I, the cellular composition of the renal cortical slices was affected in such a way as to return to normal the effectiveness of the cationic transporters per given mass.

The enhanced in vitro ion transport from IGF-I-treated rats suggests that the amount of functional tissue was increased.

Conclusion

In the above model of renal ischemia, a clear and measurable level of damage was imparted to the rabbit, which resulted in decreased renal functional ability, verified by elevated serum creatinine and urea nitrogen and decreased organic ion transport. In addition, post-ischemic weight loss seems to be a useful measure of renal function, though "post-operative" weight loss might prove to be a more apt term.

Treatment with full-sequence IGF-I at the time of insult to the kidney benefitted the rabbits in this study by providing lower serum creatinine and serum urea nitrogen levels. IGF-I-treated rabbits also demonstrated increased thymic mass, and possible though not significant reductions in weight loss. des-IGF-I-treated animals also displayed a reduction in serum urea nitrogen and normal ion concentrating abilities. Moreover, renal and splenic mass in these animals was increased, and weight loss was reduced. IGF-I and des-IGF-I are therefore potentially useful agents in the prevention or amelioration of renal ischemia in the rabbit, and could be used in other animal models.

In addition, the data show that half as many rabbits died upon treatment with des-IGF-I and IGF-I as in the control rabbits that were not so treated.

EXAMPLE III

Treatment of Rats

Introduction

This study was designed to determine whether des-IGF-I and IGF-I might prevent or at least ameliorate damage to kidneys in another species, the rat, and whether these growth factors might reduce the expected accelerated catabolism associated with renal failure.

Protocol

Three studies were conducted in which ARF was surgically induced by clamping both kidneys in anesthetized male Sprague-Dawley rats (Charles River Laboratories, Wilmington, Mass.). Anesthesia (Ketamine/xylazine, intraperitoneally, i.p.) was monitored throughout the study and supplemented to maintain a surgical plane. A pre-surgical basal blood sample was collected peri-orbitally under anesthesia and then a small subcutaneous incision was made laterally over each kidney. Then the kidney was exposed through an incision in the abdominal wall. Each kidney was then externalized, and the renal artery and vein were located and clamped for 30 or 60 minutes using a 2.5-cm Schwartz TM aneurism clip. In sham-operated animals these procedures were performed except that the kidney was not clamped. The clamps were removed, incisions sutured, and the animals allowed to recover on a heated pad. Blood chemistries were measured using a Monarch 2000 Clinical Chemistry Analyzer.

Study Design

Study 1: In the first study 16 rats were clamped for 30 minutes each. They received either 250 µg/day of des-IGF-I or its excipient (100 mM acetic acid, pH 4.5) by an Alza TM 2001 osmotic minipump placed subcutaneously, each pump being primed to operate immediately upon placement. All rats received a 50-µg injection of des-IGF-I or its excipient 90 minutes after clamps were removed. Rats were weighed and bled daily via tail vein and sacrificed in day 7.

Study 2: This study was conducted to discover the most effective clamping time in which to cause renal damage. In Study 1 it was apparent that a 30-min. clamping time produced only mild renal damage. Six rats were clamped for 30 minutes, 6 rats for 60 minutes, and the remaining 4 rats were "sham" operated controls. Rats were weighed and bled daily via tail vein and sacrificed on day 4.

Study 3: Eighteen rats were clamped for 60 minutes each and the remaining 4 rats were "sham"-operated controls. Six rats each either received 264 µg/day of des-IGF-I, 436 µg/day of IGF-I, or excipient by an Alza TM 2001 osmotic minipump placed subcutaneously, the pumps being primed to operate immediately upon placement. All rats receive a 100 µg subcutaneous injection of des-IGF-I, IGF-I, or its excipient when the clamps were removed. Rats were weighed daily and bled via tail vein through day 4 and at sacrifice on day 7.

Results

Figure 12:
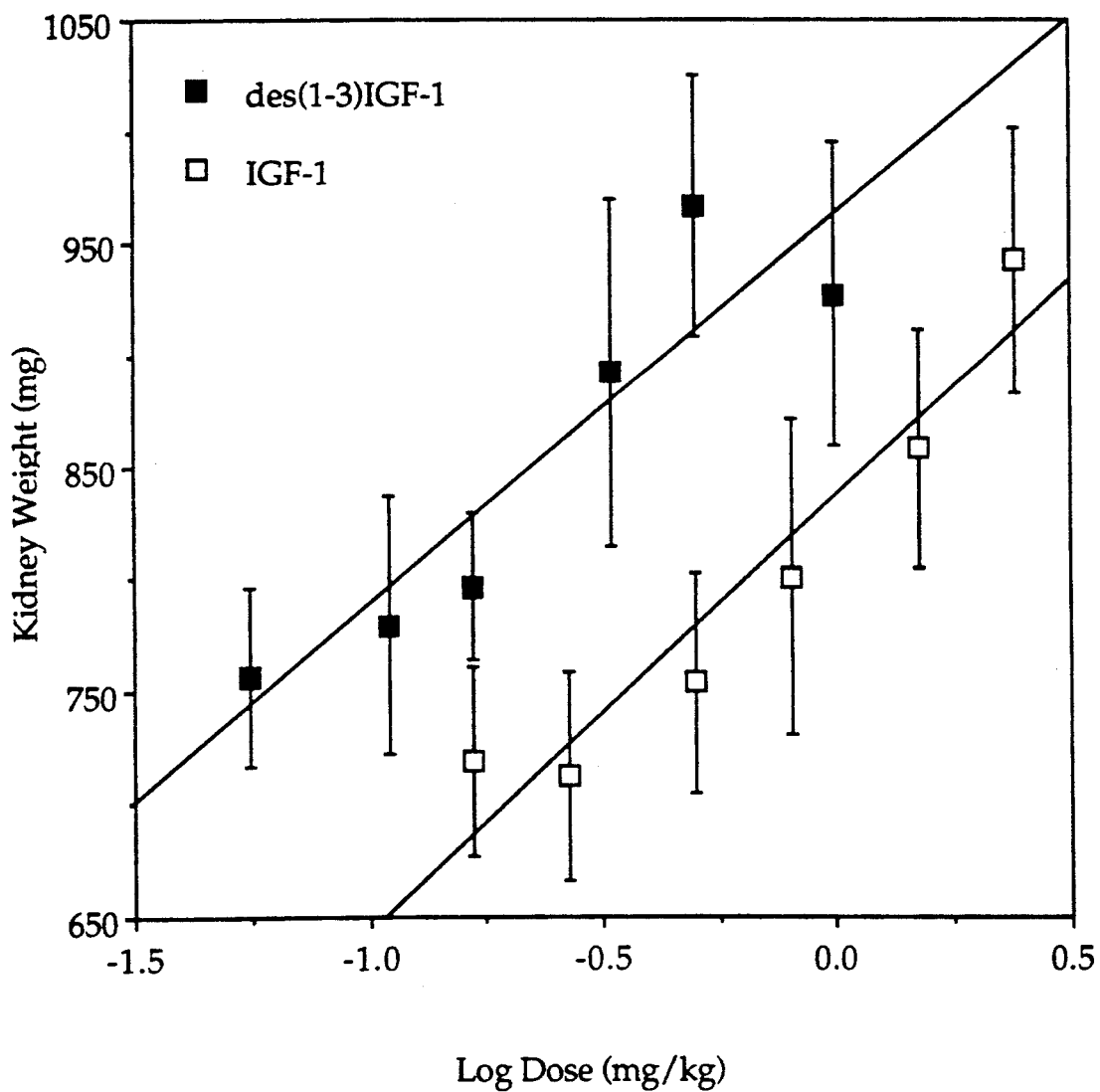
FIG. 12 is a graph of kidney weight versus dose of des-IGF-I (solid squares) and IGF-I (open squares) in hypophysectomized rats. The rats were treated for 7 days by subcutaneous minipump infusion with each of 6 doses of IGF-I or des-IGF-I and then sacrificed and the wet weights of both kidneys obtained.

FIG. 12 compares IGF-I and des-IGF-I as stimulators of renal growth in the hypophysectomized rat. The truncated IGF-I was 9-fold more potent than IGF-I as a renal growth factor. Due to these potent effects of des-IGF-I, both IGF-I and des-IGF-I were tested in the animal model of renal injury.

Figure 13:
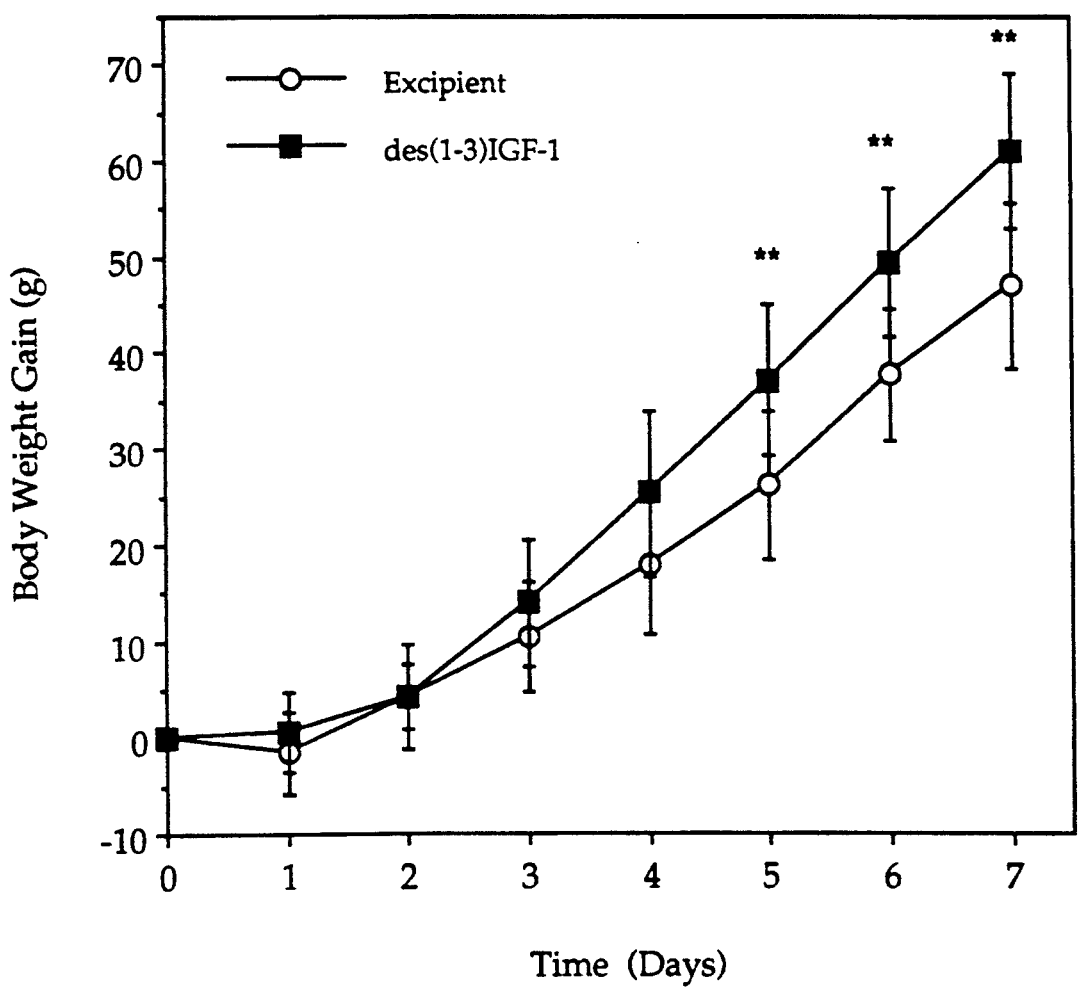
FIG. 13 is a graph of body weight gain in rats over 7 days using excipient (circles) or des-IGF-I (squares).
Figure 14:
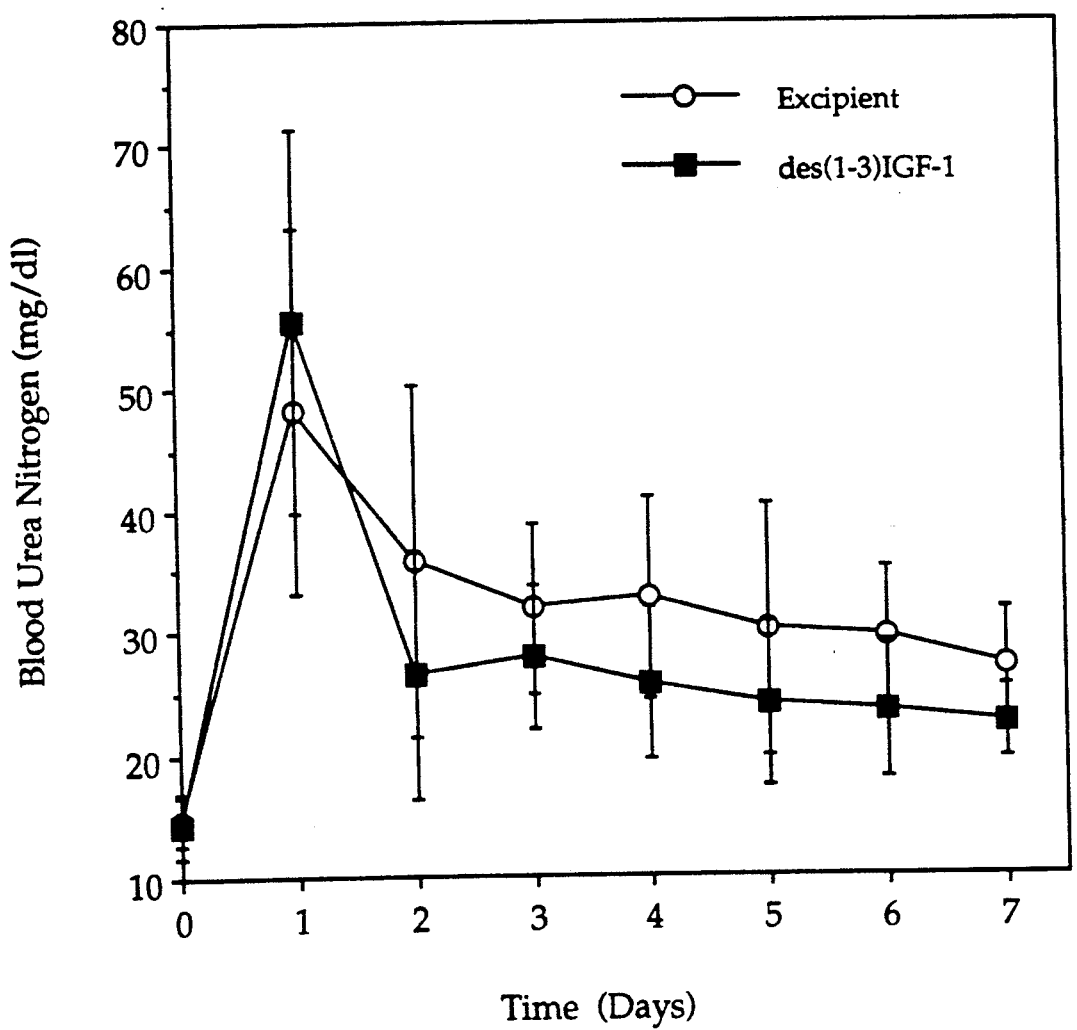
FIG. 14 is a graph of blood urea nitrogen levels in rats over 7 days using excipient (circles) or des-IGF-I (squares).
Figure 15:
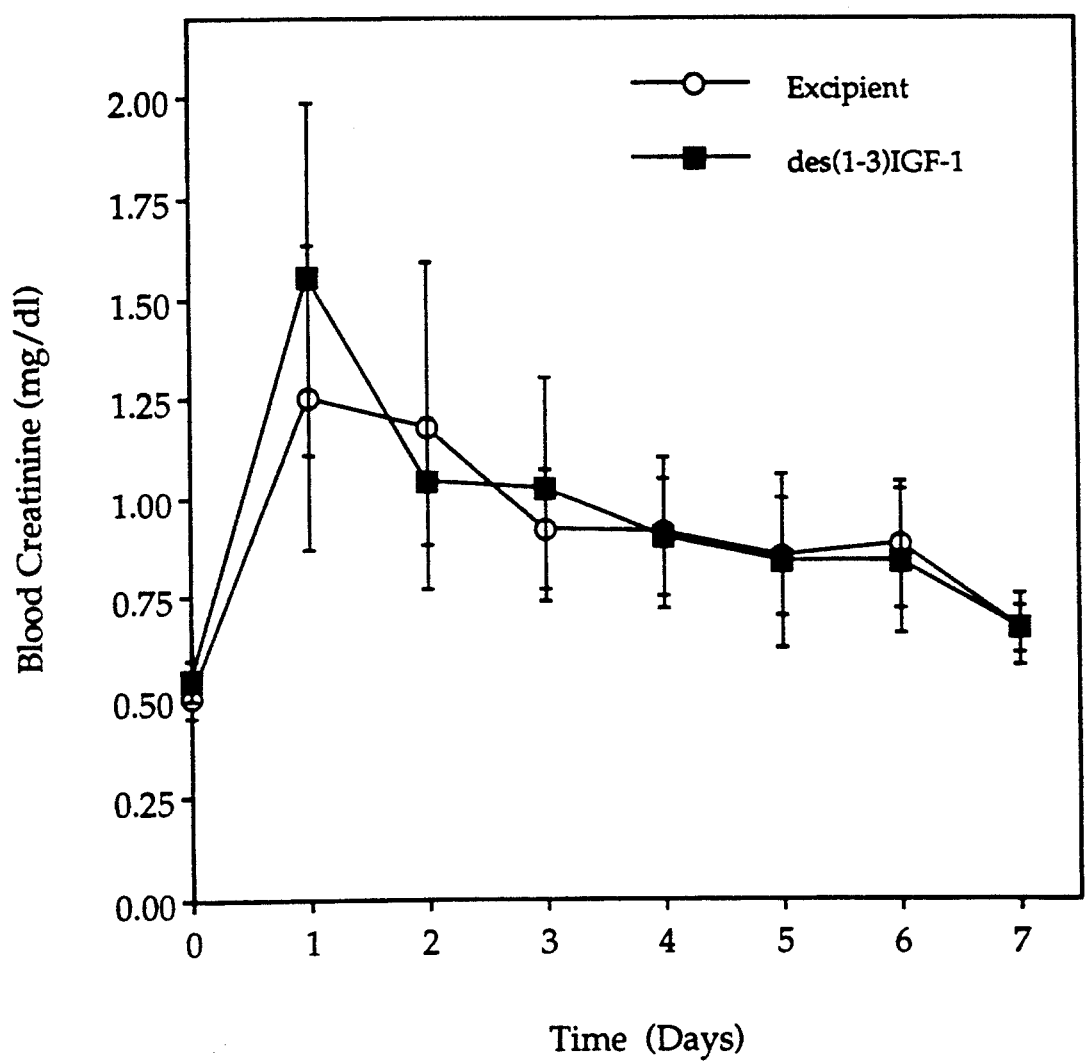
FIG. 15 is a graph of blood creatinine levels in rats over 7 days using excipient (circles) or des-IGF-I (squares).

Study 1: The course of renal failure following occlusion of the renal arteries for 30 minutes in control and des-IGF-I-treated rats is shown in FIGS. 13-15 for weight gain, BUN, and creatinine, respectively. Weight gain was significantly increased in the treated group from day 5 after injury.

The BUN rose to a similar extent in both injured groups, but was maintained at a lower level thereafter in the treated group. This effect of des-IGF-I reached statistical significance on days 6 and 7 and reflects the anabolic effect of the molecule. Serum creatinine rose and fell in a similar manner in both groups. This reflects the mild self-limiting course of the injury. Serum creatinine was taken as a measure of renal function, actually as an indirect measure of glomerular filtration rate. BUN was taken as a measure of both renal function and the catabolic state of the rats.

Figure 16:
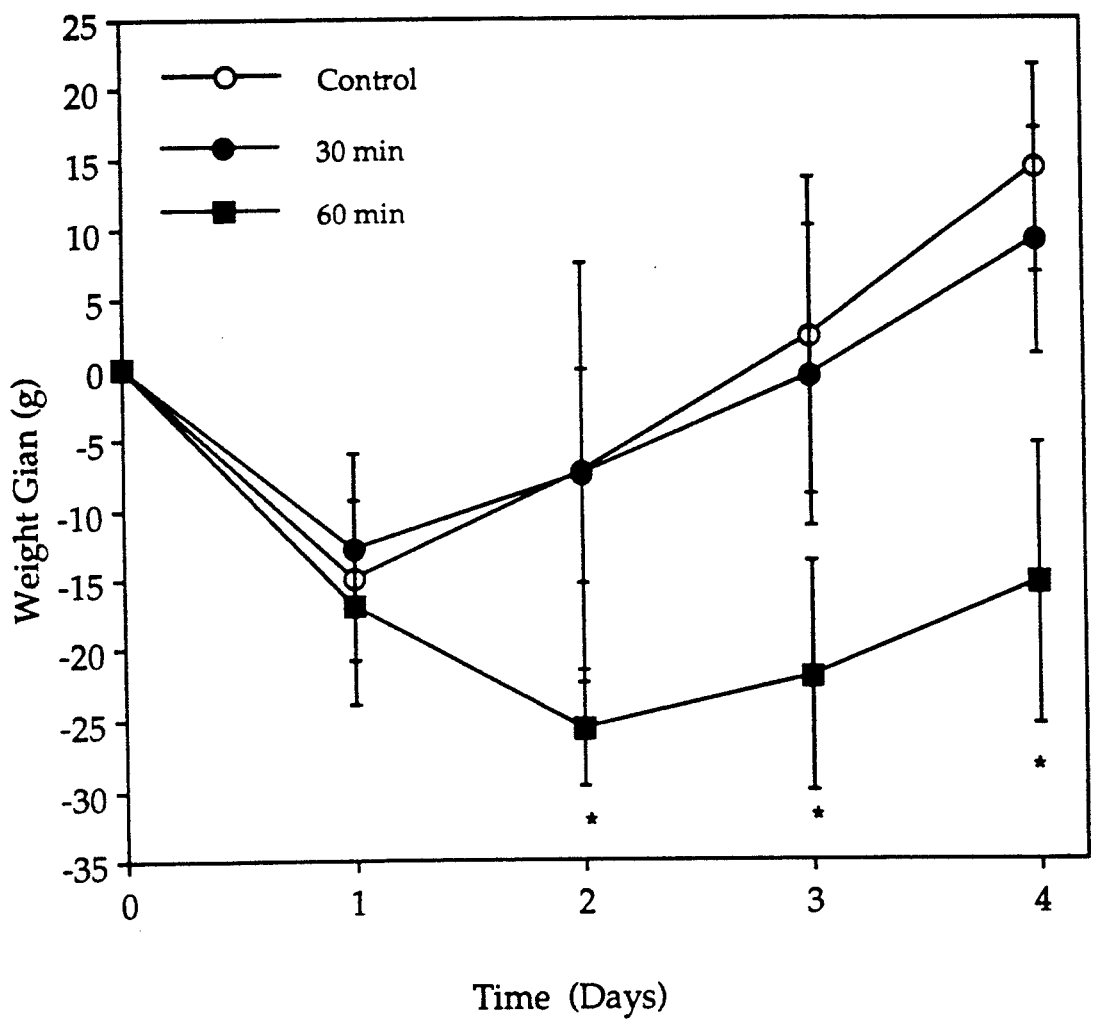
FIG. 16 is a graph of weight gain in rats over 4 days in controls (circles), after 30 min. of clamping (circles), and after 60 minutes of clamping (squares).
Figure 17:
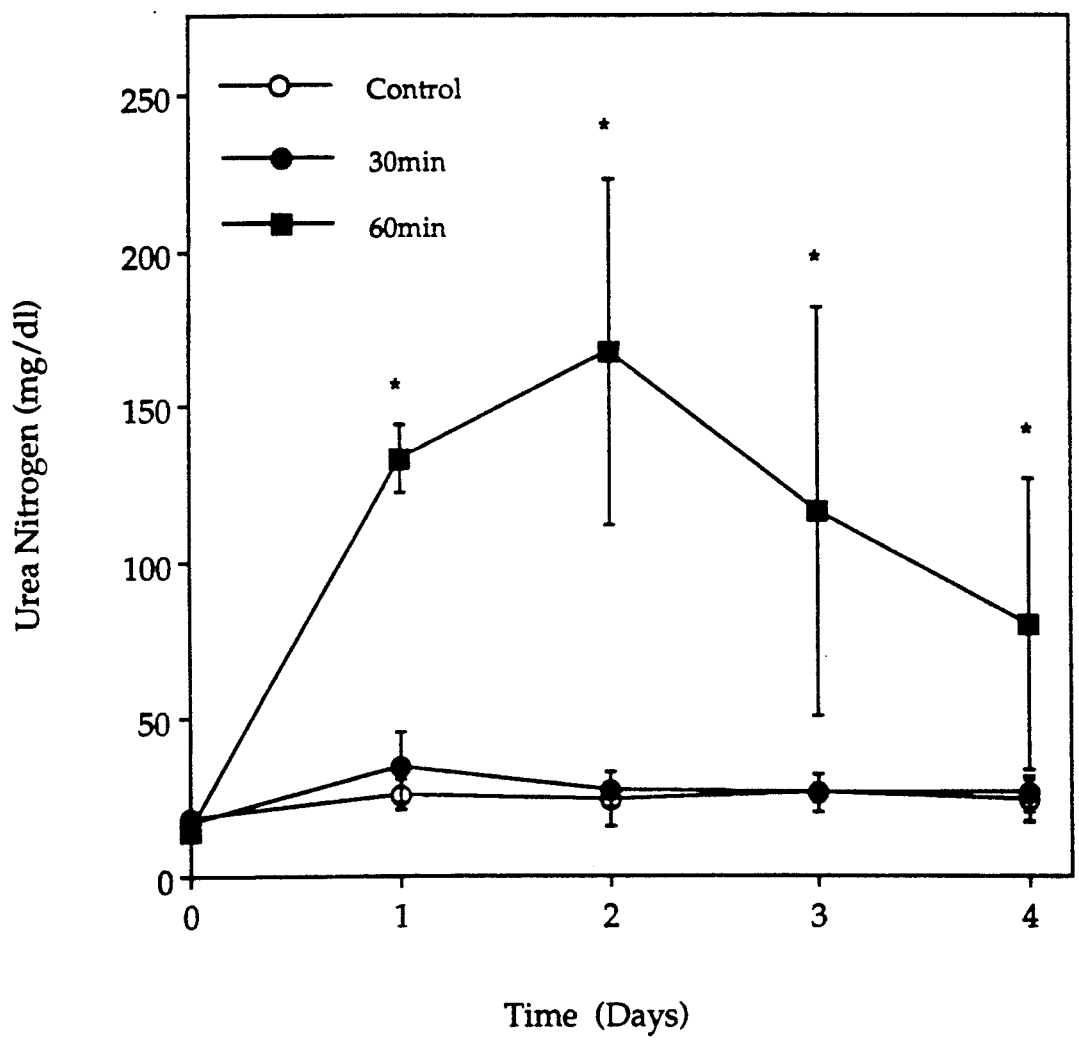
FIG. 17 is a graph of blood urea nitrogen in rats over 4 days in controls (circles), after 30 min. of clamping (circles), and after 60 minutes of clamping (squares).
Figure 18:
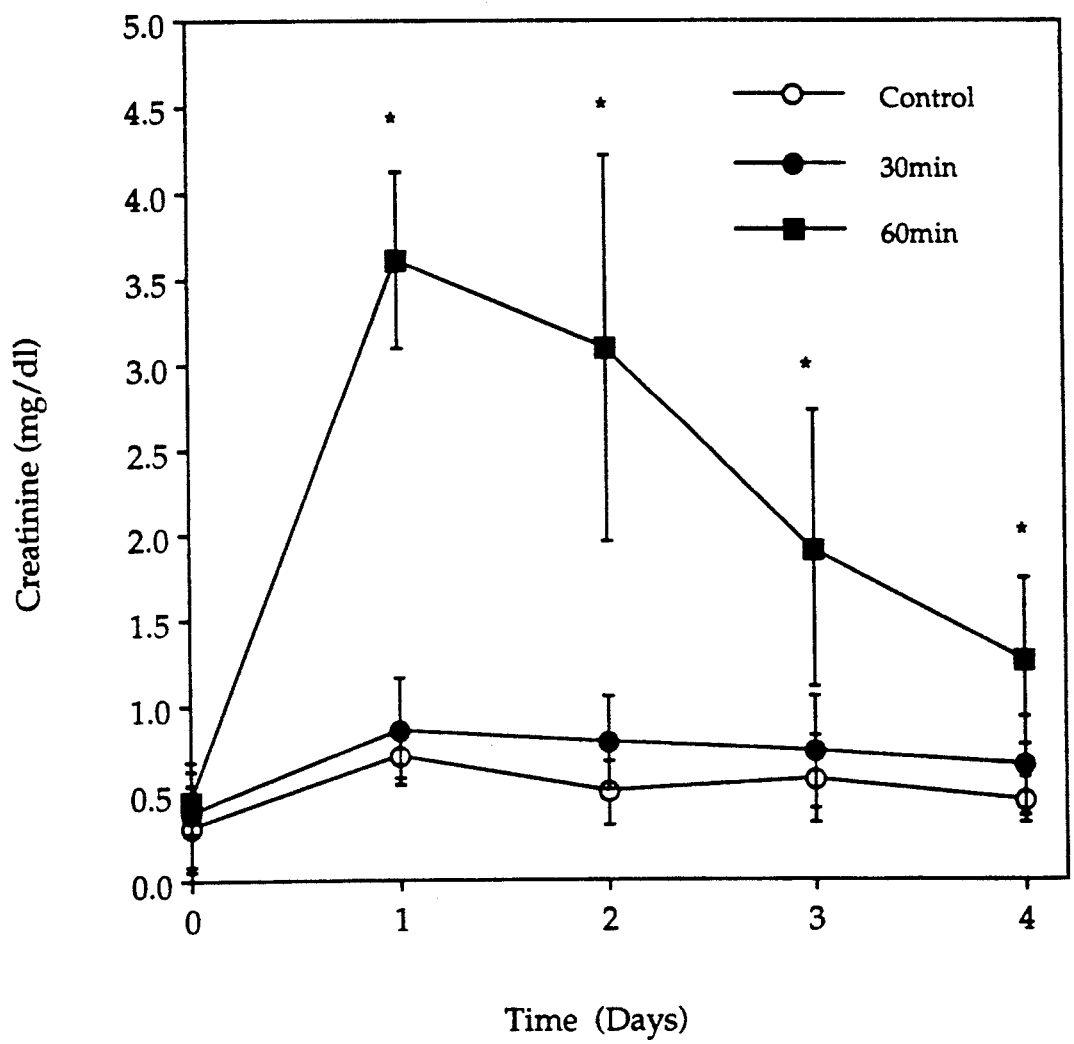
FIG. 18 is a graph of blood creatinine over 4 days in rats in controls (circles), after 30 min. of clamping (circles), and after 60 minutes of clamping (squares).

Study 2: The course of renal failure following occlusion of the renal arteries for 30 or 60 minutes was monitored to obtain a time of clamping that gave severe renal damage without being lethal. See FIGS. 16-18. Weight gain was significantly affected by surgery in all groups, but only the animals that were clamped for 60 minutes showed a maintained catabolism.

The BUN showed a dramatic rise only in the group clamped for 60 minutes. The severe nature of the effect of 60-minute clamping was also seen in the serum creatinine levels.

Clearly, clamping the renal arteries for 60 minutes produces severe renal failure compared to 30 minutes clamping, but was not lethal during the time of the study. Accordingly, the 60-minute model was used in subsequent experiments.

Figure 19:
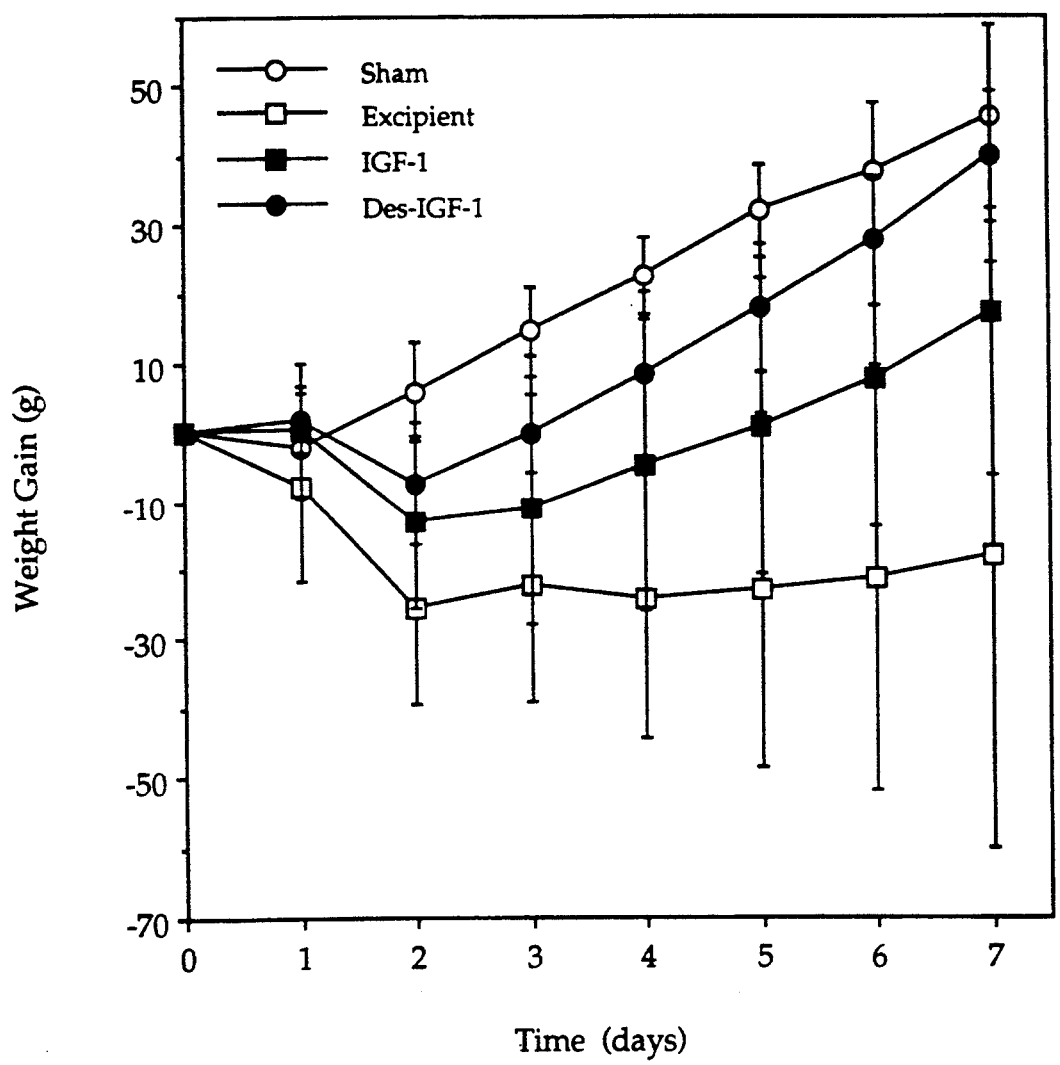
FIG. 19 is a graph of weight gain in rats over 4 days having renal injury (60 minutes of clamping) that are treated as follows: sham (open circles), clamp (open squares), clamp+IGF-I (solid squares), and clamp+des-IGF-I (solid circles).
Figure 20:
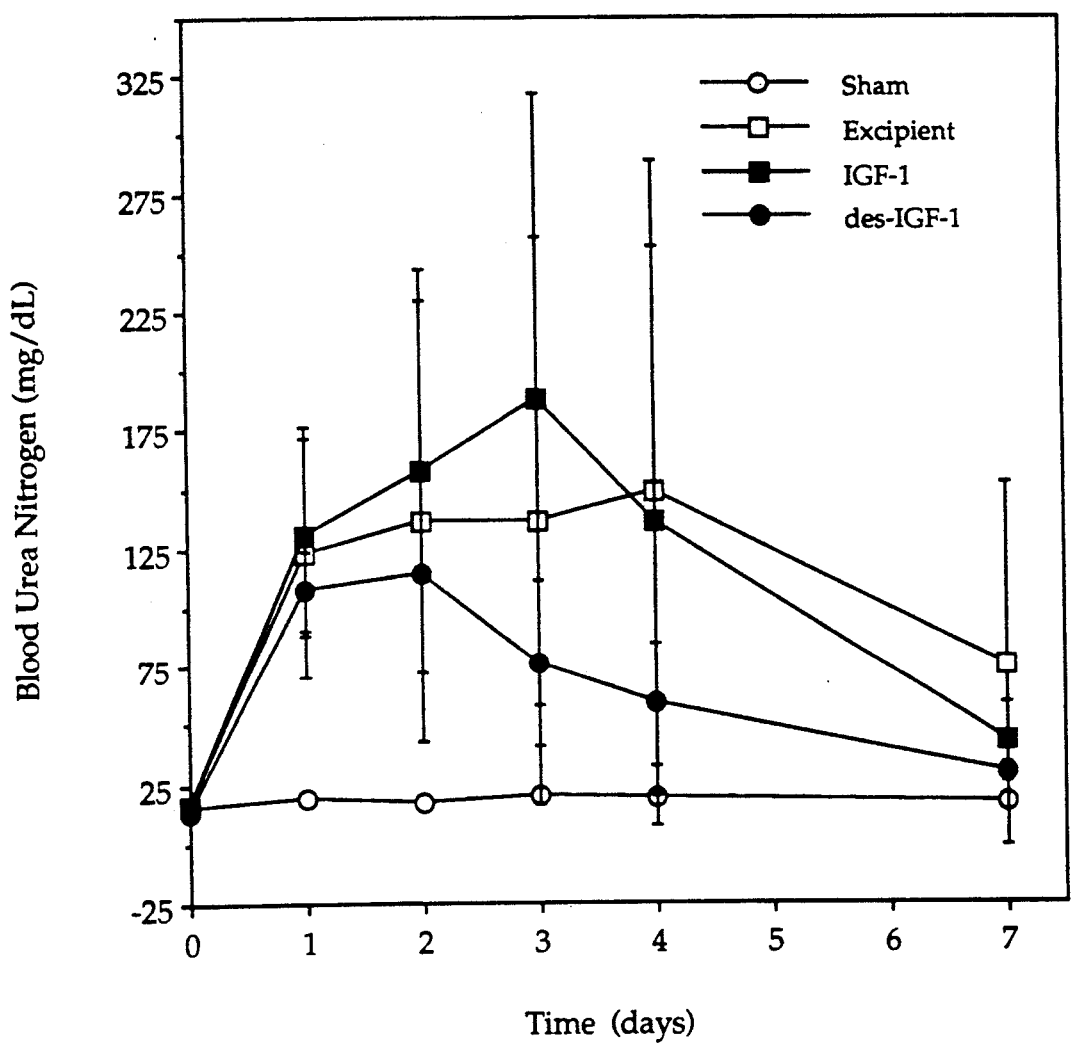
FIG. 20 is a graph of blood urea nitrogen levels in rats over 4 days having renal injury (60 minutes of clamping) that are treated as follows: sham (open circles), clamp (open squares), clamp+IGF-I (solid squares), and clamp+des-IGF-I (solid circles).
Figure 21:
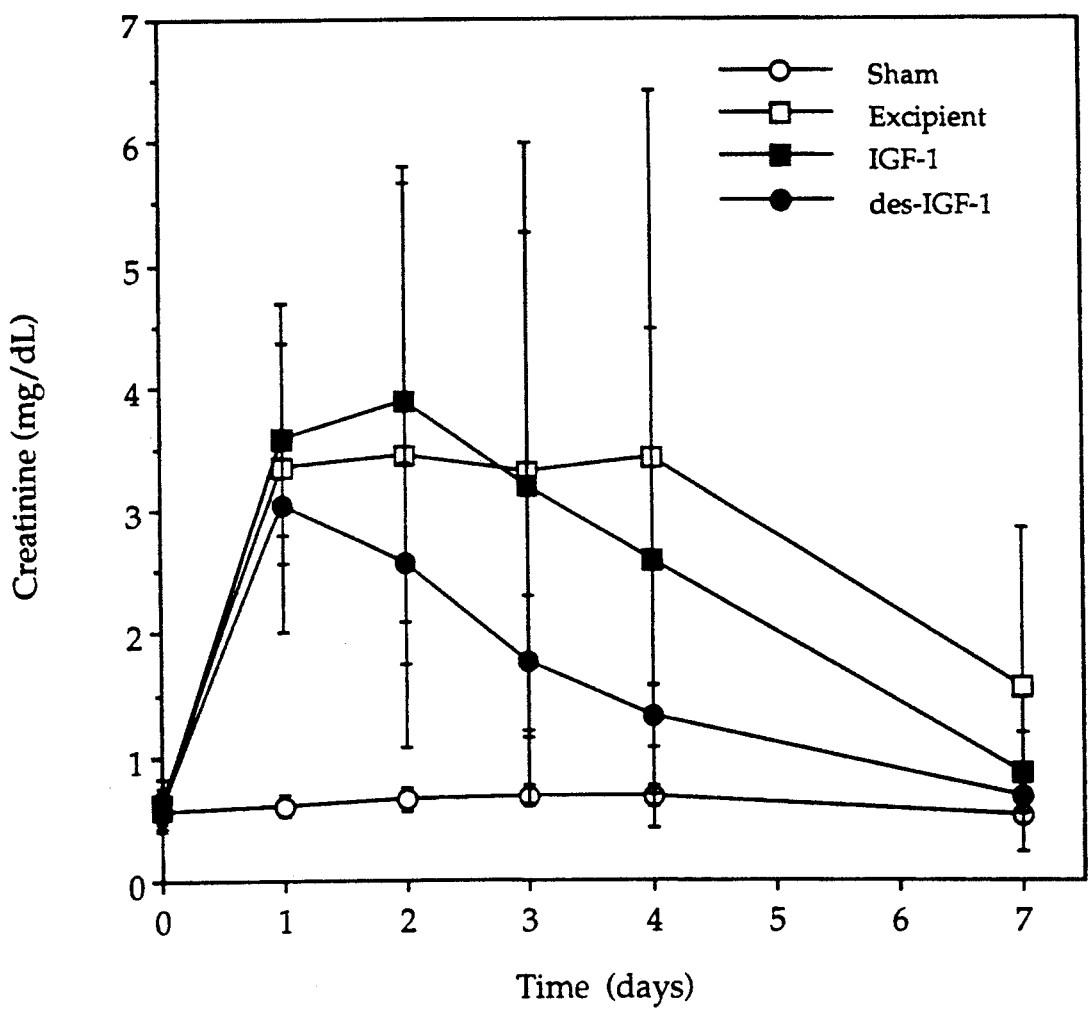
FIG. 21 is a graph of blood creatinine in rats over 4 days having renal injury (60 minutes of clamping) that are treated as follows: sham (open circles), clamp (open squares), clamp+IGF-I (solid squares), and clamp+des-IGF-I (solid circles).

Study 3: The course of renal failure following the occlusion of the renal arteries for 60 minutes was followed in animals receiving minipumps that delivered excipient, des-IGF-I, or IGF-I. See FIGS. 19-21.

The untreated renal failure rats failed to gain weight. By contrast, after 3 days of des-IGF-I therapy, weight gain occurred. In comparison, at the dose used, IGF-I had little effect.

The BUN rose to a similar extent in the clamped groups. However, des-IGF-I treatment appeared to be associated with a more rapid fall in the BUN levels.

The blood creatinine levels also rose in all clamped groups, but des-IGF-I treatment appeared to cause a faster fall compared to the other clamped groups.

SUMMARY

Clamping renal arteries for 60 minutes produced severe ARF in the rat. Treatment with des-IGF-I and IGF-I at the time of clamping appeared to prevent significant damage to kidneys subject to ischemic renal failure. Des-IGF-I appeared to exhibit anabolic growth-promoting effects in young rats with ARF, due at least partially to the growth factor accelerating the recovery of renal function. At the dose used, IGF-I did not have the marked effects on renal recovery or body growth that were seen with a lower dose of des-IGF-I. It is expected, however, that adjustment in the dose of IGF-I employed or in the mode of administration would produce a greater effect on renal recovery in the rat, since it displayed such effect in the rabbit model.

These results suggest that IGF-I acts as a prophylactic drug for mammals at risk for ARF to prevent significant renal damage from occurring. IGF-I has characteristics that in the long run lead to greater effectiveness in treating patients.

It would be reasonably expected that the rabbit and rat data herein may be extrapolated to horses, cows, and other mammals, correcting for the body weight of the mammal in accordance with recognized veterinary and clinical procedures. Using standard protocols and procedures, the veterinarian or clinician will be able to adjust the doses, scheduling, and mode of administration of IGF-I and its variants to achieve maximal effects in the desired mammal being treated. Humans are believed to respond in this manner as well.

What is claimed is:

1. A method for prophylaxis of acute renal damage or failure in a mammal at risk for acute renal damage or failure comprising initiating administration to the mammal of an effective amount of IGF-I before or at the time that acute renal damage is expected to occur or is occurring, but not initiating administration after acute renal damage is expected to occur or has occurred.

2. The method of claim 1 wherein the mammal is a human.

3. The method of claim 1 wherein the effective amount of IGF-I is 0.01 to 1 mg/kg/day.

4. The method of claim 1 wherein the administration of IGF-I is continued after acute renal damage is expected to occur or is occurring.

5. The method of claim 1 wherein the acute renal failure is due to ischemic renal injury.

6. The method of claim 2 wherein the human is undergoing cardiac surgery.

7. The method of claim 1 wherein the mammal is undergoing renal transplantation.

8. The method of claim 7 wherein the IGF-I is administered before the transplantation.

9. The method of claim 1 wherein the acute renal failure is due to nephrotoxic damage.

10. The method of claim 1 further comprising administering, in addition to the IGF-I, an effective amount of growth hormone to the mammal.

* * * * *